United States Patent
Claps

(10) Patent No.: US 9,157,858 B2
(45) Date of Patent: Oct. 13, 2015

(54) TIME-RESOLVED SPECTROSCOPY SYSTEM AND METHODS FOR MULTIPLE-SPECIES ANALYSIS IN FLUORESCENCE AND CAVITY-RINGDOWN APPLICATIONS

(71) Applicant: Ricardo J. Claps, Clovis, CA (US)

(72) Inventor: Ricardo J. Claps, Clovis, CA (US)

( * ) Notice: Subject to any disclaimer, the term of this patent is extended or adjusted under 35 U.S.C. 154(b) by 175 days.

(21) Appl. No.: 13/848,723

(22) Filed: Mar. 21, 2013

(65) Prior Publication Data

US 2013/0218479 A1 Aug. 22, 2013

Related U.S. Application Data

(63) Continuation of application No. 12/697,227, filed on Jan. 30, 2010, now Pat. No. 8,405,827, which is a continuation-in-part of application No. 11/603,939, filed on Nov. 21, 2006, now Pat. No. 7,679,745.

(51) Int. Cl.
| | |
|---|---|
| *G01N 21/00* | (2006.01) |
| *G01N 21/64* | (2006.01) |
| *G01J 3/02* | (2006.01) |
| *G01J 3/10* | (2006.01) |
| *G01J 3/28* | (2006.01) |
| *G01J 3/44* | (2006.01) |
| *G06F 17/10* | (2006.01) |

(52) U.S. Cl.
CPC . *G01N 21/64* (2013.01); *G01J 3/02* (2013.01); *G01J 3/0205* (2013.01); *G01J 3/0218* (2013.01); *G01J 3/0256* (2013.01); *G01J 3/10* (2013.01); *G01J 3/2889* (2013.01); *G01J 3/4406* (2013.01); *G01N 21/6408* (2013.01); *G06F 17/10* (2013.01)

(58) Field of Classification Search
CPC ........ G01N 21/39; G01N 21/3504; G01J 3/42
See application file for complete search history.

(56) References Cited

U.S. PATENT DOCUMENTS

| 4,164,373 A * | 8/1979 | Schuss et al. ............... 356/316 |
|---|---|---|
| 6,377,350 B1 * | 4/2002 | Paldus et al. ................ 356/454 |
| 2003/0189711 A1* | 10/2003 | Orr et al. ..................... 356/484 |
| 2006/0072110 A1* | 4/2006 | Lodder et al. ............... 356/419 |
| 2007/0167839 A1* | 7/2007 | Carver ......................... 600/476 |

OTHER PUBLICATIONS

Li et al., "Multichannel-fiber ringdown sensor based on time-division multiplexing", Dec. 15, 2008, Optics Letters, vol. 33, No. 24, pp. 3022-3024.*

* cited by examiner

*Primary Examiner* — Kara E Geisel

(57) ABSTRACT

A time-resolved spectroscopy system employing a time-division multiplexing optical device with no dispersive optical elements to perform lifetime and concentration measurements in multi-species samples, is disclosed. Some examples include fluorescence and cavity ring-down spectroscopy. The system is unique in its compactness and simplicity of operation. In one embodiment, the system makes use of only one photo-detector and an efficient linear regression algorithm. The system offers a measurement time for multiple species measurements of less than 1 s. The system can also be used to perform fluorescence correlation spectroscopy and fluorescence cross-correlation spectroscopy. Four methods to deconvolve a multi-component, exponentially decaying optical signal such as obtained with the system disclosed here, are presented. These methods may be applied to the measurement of fluorescence decay lifetimes and cavity ring-down times, the latter used extensively for the measurement of gas and trace-gas concentrations in complex mixtures, via absorption spectroscopy.

11 Claims, 21 Drawing Sheets

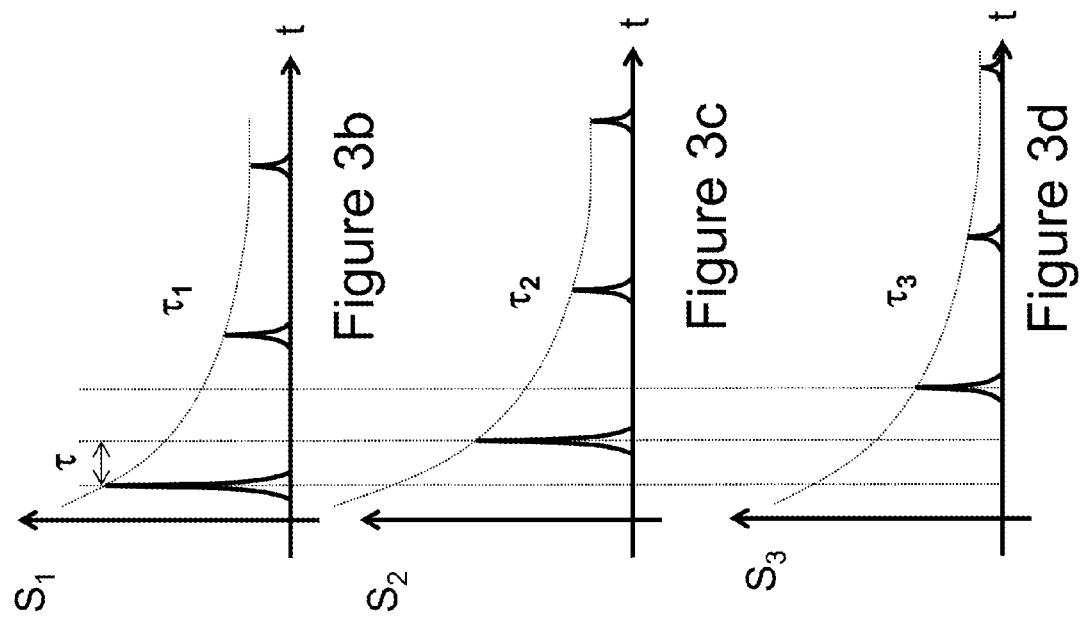

TIME-RESOLVED SPECTROSCOPY SYSTEM AND METHODS FOR MULTIPLE-SPECIES ANALYSIS IN FLUORESCENCE AND CAVITY-RINGDOWN APPLICATIONS

CROSS-REFERENCE TO RELATED APPLICATIONS

The present application is a continuation of and claims priority to U.S. patent application Ser. No. 12/697,227, filed on Jan. 30, 2010, now U.S. Pat. No. 8,405,827, to be issued on Mar. 26, 2013, incorporated herein by reference in its entirety, for all purposes, and which is a continuation in part of and claims priority to U.S. patent application Ser. No. 11/603,939, filed on Nov. 21, 2006, now U.S. Pat. No. 7,679,745, which is incorporated herein by reference in its entirety, for all purposes.

RELATED PATENTS

This application is related to U.S. Pat. No. 7,298,538, issued on Nov. 20, 2007, and U.S. Pat. No. 7,602,488, issued on Oct. 13, 2009, which are incorporated herein by reference in their entirety.

FIELD OF THE INVENTION

This invention relates to a time-resolved spectrometer system that is capable of measuring samples with multiple components simultaneously. The system is environmentally rugged, has low cost, and can be used in field applications where other spectroscopic techniques could not be implemented.

BACKGROUND OF THE INVENTION

Time-resolved spectroscopy is a widely used technique in the Biological sciences. In fluorescence spectroscopy, light at a specific frequency is absorbed by a given molecule or fluorescent entity (also called fluorophore), exciting its electronic state. The fluorescent entity then emits light at a slightly different frequency, as the fluorophore returns to the original ground state. Fluorescence spectroscopy is analogous to Raman spectroscopy in that a pump light excitation induces the emission of Stokes light, shifted to a lower frequency relative to the pump light. However, fluorescence requires the absorption of the pump light of a specific frequency, the frequency depending on the electronic system of the fluorescent entity. Also, contrary to Raman scattering, typical Stokes shifts for fluorescence phenomena are a few 10's of nm apart from the pump light, which complicates the cross-talk between the pump light and the Stokes signals at the detection level. Furthermore, as opposed to Raman scattering, which is essentially instantaneous, fluorescence emission takes place across a wide range of lifetimes, within a few ns or up to a few ms, depending on the fluorophore.

There are other types of time-resolved spectroscopy techniques widely used in biological applications and trace-gas sensing, such as Cavity Ring-Down Spectroscopy (CRDS).

In general, time-resolved spectroscopy techniques are mostly limited to laboratory environments due to the following reasons:

1) Short lifetime measurement techniques require the use of expensive and delicate equipment: pulsed pump lasers and state-of-the-art synchronized photo-detection schemes.

2) Time-resolved spectroscopy instrumentation is bulky due to the use of specially aligned optics, and high-end, photo-detector arrays.

3) Conventional time-resolved techniques such as fluorescence require the use of high performance optical filters to mitigate the cross-talk between pump and Stokes fluorescence signals, between the Stokes signals from different fluorophores, or the absorption signal of different molecules. This adds to the cost of the instrument and its complexity, reducing the signal collection efficiency.

4) Due to the extra complexity and cross-talk added by the optical filtering procedures, only small number of target substances can be analyzed simultaneously (3 or 4 at a time).

5) In fluorescence lifetime measurements, fluorophore concentration values are normally disregarded, as the measurement technique is only involved with relative changes of the signal in time. Also, the analytical complexity of deriving both lifetime and concentration values increases rapidly with the number of targets being analyzed. As a result, current lifetime fluorescent techniques are limited to fixed concentration measurements for a few target substances (2, 3 or 4).

6) Due to the close spectral proximity between the pump and Stokes signals in fluorescence spectra, and between Stokes signals from different fluorophores, high-performance optical filtering techniques are required. This increases cost and complexity of typical fluorescence devices.

In view of the above, there is a need for a time-resolved spectroscopy system that can be implemented in field applications under harsh environmental conditions. These applications usually require measurement of multiple targets (10 to 25) simultaneously. A complete measurement and sample assessment needs to be performed in a time frame of 1 s or less. Such a device would not only find new applications but also enhance current technologies like DNA sequencing and fluorescence imaging microscopy.

SUMMARY OF THE INVENTION

In accordance with the present invention a device such as a RadiaLight® switch is used for the implementation of a time-resolved spectroscopy system that has the quality of being compact, rugged and fast (with measurement times of less than 1 s). In some embodiments, the instrument can perform single species analysis; some embodiments may include multiple species analysis (10 to 25, or more), with the capability of measuring radiation intensity and decay lifetimes for each of the different species or compounds included in a sample.

An embodiment of the system uses the RadiaLight® switch as a time-division multiplexing device that delivers a pulsed fluorescent pump light sequentially into one or more samples. At the same time, the RadiaLight® device collects the fluorescence produced by each sample in a synchronized sequence of pulses, thus providing a precise temporal profile of the signal induced by the pump pulse. In some embodiments, the device performs time-resolved fluorescence (TRF) of a sample with a plurality of components, each of them associated with a fluorophore that has a distinct decay time that lies within the time range detectable by the device.

In some embodiments of the present invention, the time-division multiplexing capability of the device is combined with the ability to use a plurality of optical band-pass filters for each optical channel. These embodiments may increase the number of components that the system can analyze simultaneously by using fluorophores that have different lifetimes and different emission spectra.

Another embodiment of the invention makes use of device architecture analogous to that disclosed in U.S. Pat. No. 7,602,488, assigned to Neptec Optical Solutions, Inc., incorporated herein by reference in its entirety. In this embodiment, the fluorescence pump light is not pulsed by the time-division optical multiplexer device, but illuminates the sample continuously. The fluorescence radiation is collected and passed through the time-division optical multiplexer, which directs the radiation into a sensitive photo-detector as a sequence of pulses, each of which has been spectrally filtered in order to separate the Stokes signal from different fluorophores. In this embodiment, the fluorescent decay lifetime of the fluorophores has to be faster than the intra-optical channel period of measurement, also known as dwell time of the device ($\Delta T$). In this embodiment, the present invention can be used to perform fluorescence correlation spectroscopy (FCS) and fluorescence cross-correlation spectroscopy (FCCS).

Some embodiments of the present invention may use a time-division multiplexing device in combination with a light source and a detector to measure the decay times of radiation that may be emitted by some compounds in the sample, or transmitted and absorbed by some compounds in the sample. Therefore, the sample may include compounds that emit light, such as fluorescent emitters or fluorophores, and also compounds that absorb light. The absorption and emission of light by the compounds included in the sample may occur at different frequencies, or some of the emission spectral ranges and absorption spectral range may overlap.

In summary, in accordance with some embodiments of the present invention a device is provided that performs time-resolved spectroscopy enabling multiple-component monitoring with environmental ruggedness and enhanced processing speed. The device has the following unique properties:

Processes and analyzes multiple component samples within a total measurement time of 1 ms to 100 ms.

The ability to use a single ultra-sensitive photo-detector to enhance the sensitivity at high speed.

Provides a simple time-calibration of the optical signal, therefore improving the accuracy of data collection at a reduced cost.

Can quantitatively determine a mixture composed of multiple components (20-25+components), simultaneously.

Is field-deployable, suitable to be used in moving vehicles and aircraft, and hostile physical environments, with no degraded performance.

Can operate in any given orientation relative to the ground, with no need for readjustments due to gravity.

Provides a wide bandwidth of detection, from 300 nm to 1.0 µm, or 900 nm to 1.5 µm, depending on the photo-detector design.

Eliminates the use of gratings, prisms, and other dispersive elements that have high loss, are expensive, and extremely sensitive to alignment.

In some embodiments of the invention, the use of optical filters is completely eliminated in the device.

Uses a single photosensitive element, replacing the need for photo-detector arrays and CCD cameras, and simplifying data collection schemes.

Uses a linear regression algorithm for data processing, reducing the number of data points to be handled by an order of magnitude.

Uses an algorithm that incorporates an auxiliary time-dependent function, to measure concentrations and emission/transmission decay lifetimes of multiple compounds, simultaneously.

Uses an algorithm that incorporates a discrete Laplace Transform technique, and a step-speed scan technique, to measure concentrations and emission/transmission decay lifetimes of multiple compounds, simultaneously.

Uses an algorithm that incorporates a discrete Laplace Transform technique, and a continuous-speed scan technique, to measure concentrations and emission/transmission decay lifetimes of multiple compounds, simultaneously.

Allows for a method to perform real-time, non-invasive temperature measurements of samples, in-vivo or for other applications, based on Fluorescence-lifetime spectroscopy.

Allows for a method to determine multi-component concentrations in a given sample, using lifetime spectroscopy and linear regression techniques. In this methodology, the sample can be a solid, a powder, a liquid, or a gas.

Potential applications include the development of in-vivo blood gas sensors, based on Fluorescence life-time measurement techniques: $CO_2$, $O_2$, pH, the development of oxygen sensors for industrial applications such as semiconductor manufacturing and combustion diagnostics, and the development of in-vivo, time-resolved metal ion sensors such as $Cu^{+2}$, $Na^+$, $Ca^+$, which are relevant for physiological diagnostics.

This invention will be more fully understood in view of the following drawings taken together with the following detailed description.

BRIEF DESCRIPTION OF THE DRAWINGS

The accompanying drawings, which are incorporated in, and constitute a part of this specification illustrate exemplary implementations and embodiments of the invention and, together with the description, serve to explain principles of the inventions as follows:

FIG. 3a shows an embodiment of this invention using a multiplicity of optical filters 3-1 to 3-9 in order to perform lifetime measurements of different emitting compounds ($S_1$, $S_2$, $S_3$). The filters are arranged in sequence such that three (3) consecutive optical channels correspond to the three different substances represented in the FIG. 3a. In FIG. 3a, the sequence of three different filters is repeated three times. Other numbers of optical channels can be used in this embodiment if desired.

FIGS. 3b, 3c, and 3d show the waveforms as detected by the photo-detector or photo-detectors attached to the optical channels 2-1 to 2-9.

DETAILED DESCRIPTION OF THE INVENTION

The following detailed description is meant to be illustrative only and not limiting. Other embodiments of this invention will be obvious to those skilled in the art in view of this description.

In accordance with this invention a time-resolved spectroscopy system architecture is provided that combines a high-speed time-division optical sampling engine with a unique data processing algorithm, discrete Principal Component Analysis (dPCA), in order to produce time-resolved, accurate emission and transmission measurements with low signal levels. A variety of embodiments are provided to implement the invention. Some embodiments of the invention significantly decrease sample processing time, while increasing the number of compounds that can be processed at one time for a given sample. Some embodiments of this invention improve the environmental ruggedness of the device while significantly reducing the implementation cost.

Figure 1A:
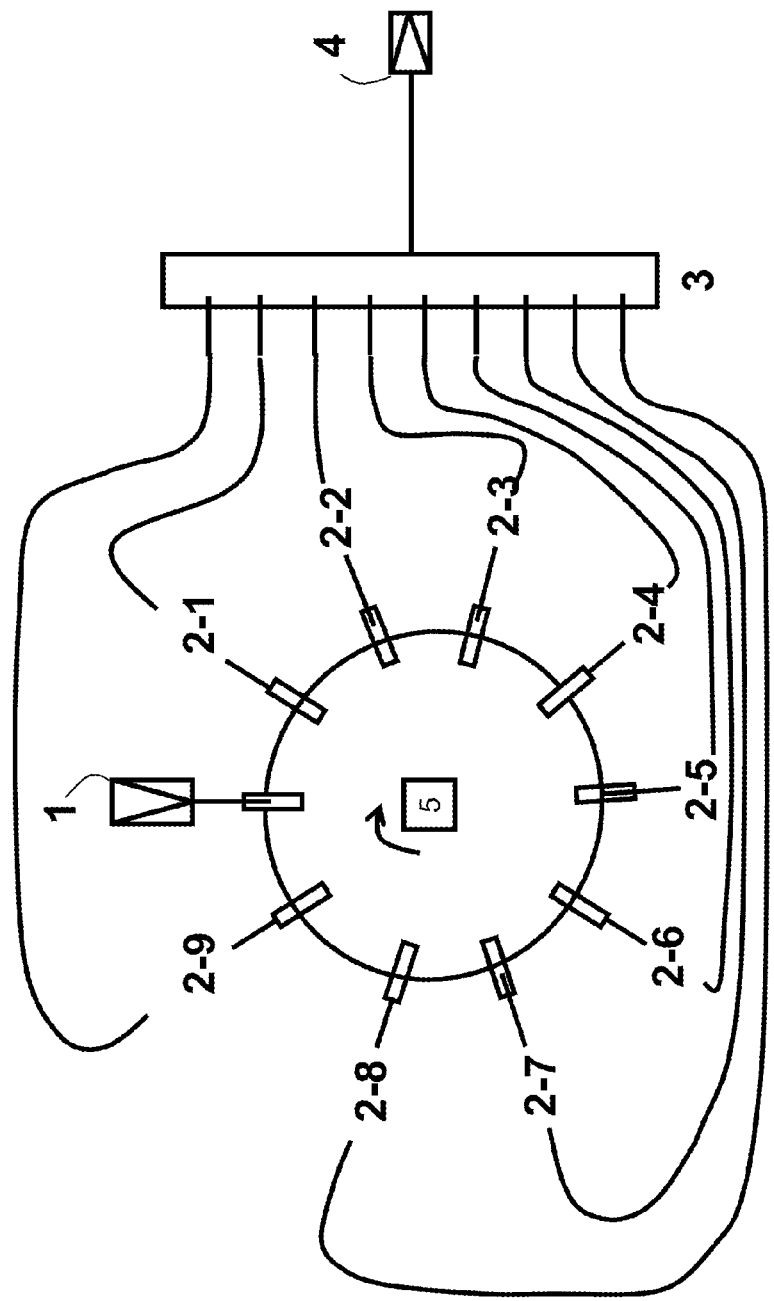
FIGS. 1a and 1b show schematically top and side views of one embodiment of the invention, respectively, using a time-division multiplexer, an optical pump source, and a photo-detecting element.
Figure 1B:
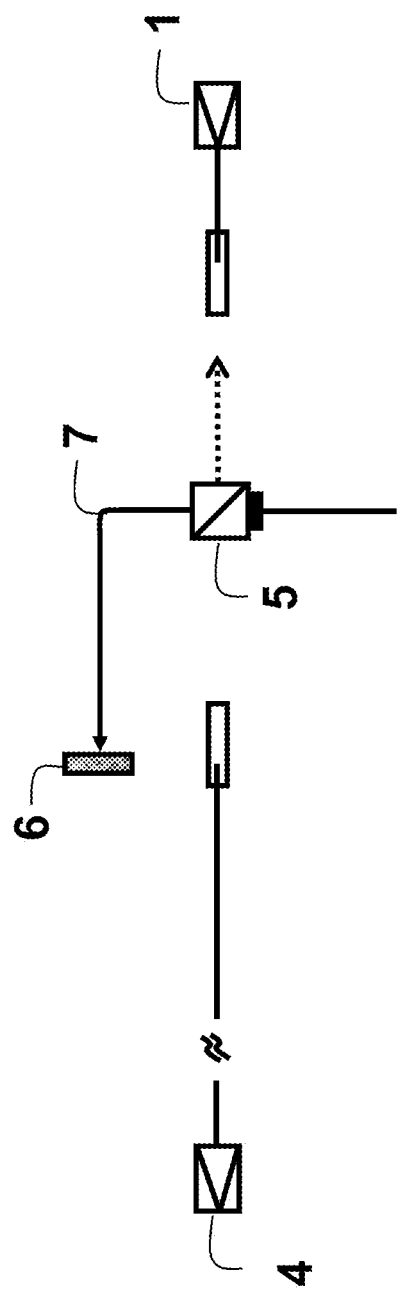

Referring to FIGS. 1a and 1b, one embodiment of this invention employs a rotary switch such as disclosed in U.S. Pat. No. 7,298,538 (RadiaLight®), hereby incorporated by reference in its entirety. The rotary switch acts as a time-division multiplexing device. In the embodiment shown in FIGS. 1a and 1b, light from a pump laser 1—or other light source such as a SLED (a "super-luminescent light emitting diode"—or a gas emission lamp using halogen gases or mercury or equivalent) is transmitted along a path 1a to a rotating prism 5 containing a reflecting surface 5a which reflects the light from laser 1 along a waveguide 7 to illuminate a material sample 6 to be interrogated. Sample 6 contains a light emitting compound which, in response to incident light from laser 1, emits radiation back along waveguide 7 to rotating prism 5. Light emitted from the sample—called information light or in some embodiments, "Stokes radiation"—contains specific information about the chemical and physical make up of the material being interrogated. Hereafter, the term "Stokes radiation" will be used to mean the same as "information light." In some embodiments of the present invention, emitted radiation is fluorescent light emitted from the sample as a result of light from source 1 impinging on sample 6.

In the embodiment of FIGS. 1a and 1b, the optical delivery of the light from the illumination source and the optical collection from sample 6 of the information light are performed through the same fiber 7—in some embodiments called a "waveguide". As shown in FIGS. 1a and 1b, the light from source 1 to be incident on sample 6 is transmitted to optical fiber 7, through one of the optical channels of the RadiaLight® time division multiplexer 50. In this manner, even if the light source 1 is operating in continuous mode (CW), the pump light in the delivery optical channel 7 has a pulsed time profile because prism 5 is rotating at a selected speed driven by a precision electric motor. In some embodiments of the present invention, this motor can be any of several well known commercially available motors of a type used, for example, in gyroscopes. In one embodiment, this motor can rotate speeds such as 200,000 RPM or more, if required.

Information light is emitted from sample 6 throughout a period of time comparable to the emission lifetime, $\tau_0$. The information light is carried back from sample 6 into the RadiaLight® device 50 by waveguide 7. Since there is a time delay, τ, between the pump pulse from laser 1 and the signal carried back from sample 6 to rotating prism 5, there is no need to have a filter or a circulator in series with waveguide 7. In most fluorescence spectrometers, as well as in any typical Raman device and other time-resolved spectrometry systems, an optical filter is necessary in order to block the pump light from the photo-detector in the instrument. In multiplexing device 50 reflecting prism 5 rotates about axis 5b which is perpendicular to the path 1a along which light from laser 1 is sent to prism 5. Because prism 5 rotates at a selected rotational speed, the information light from sample 6 which travels back along waveguide 7 to prism 5 is reflected by the mirror 5a in prism 5 to one or more optical channels 2-i (where 'i' is an integer given by 1≤i≤I where I is the maximum number of optical channels) located about the circumferential perimeter of stationary platform 5c, at a different time than that at which the initial illuminating pulse from pump laser 1 hits the sample 6. Platform 5c holds a plurality of optical channels 2-i (shown in FIG. 1b as waveguides 2-1 to 2-9) each of which receives a portion of the signal emitted from sample 6 as prism 5 rotates. Of course, the strength of the signal emitted from sample 6 will decrease with time. The rate of decrease will depend upon the lifetime of the emitter used with sample 6 and can vary from as short as a few nanoseconds to as much as several milliseconds or even seconds.

Some embodiments of the present invention include absorbing compounds in the sample, so that the light transmitted through the sample will have a time-decaying profile. The lifetime of such profile will be dependent on the rate of absorption of radiation by the compound, which is proportional to the concentration of said compound in the sample. Measurement of the decay lifetime of the transmitted signal will therefore indicate the concentration of absorbing compounds in the sample.

In some embodiments of the present invention, the RadiaLight® optical switch includes a motor-driven, rotating prism 5 is described in detail in U.S. Pat. No. 7,298,538, incorporated herein by reference in its entirety.

Multiplexer 3 (which might be based on single mode fiber, multi-mode fiber, or a photonic crystal fiber (PCF) depending on the desired numerical aperture, bandwidth and transmission loss of the device) will pass the signal being transmitted on the corresponding fiber 2-i when information light reflected from the rotating prism 5 impacts the corresponding waveguide, 2-i.

Figure 2:
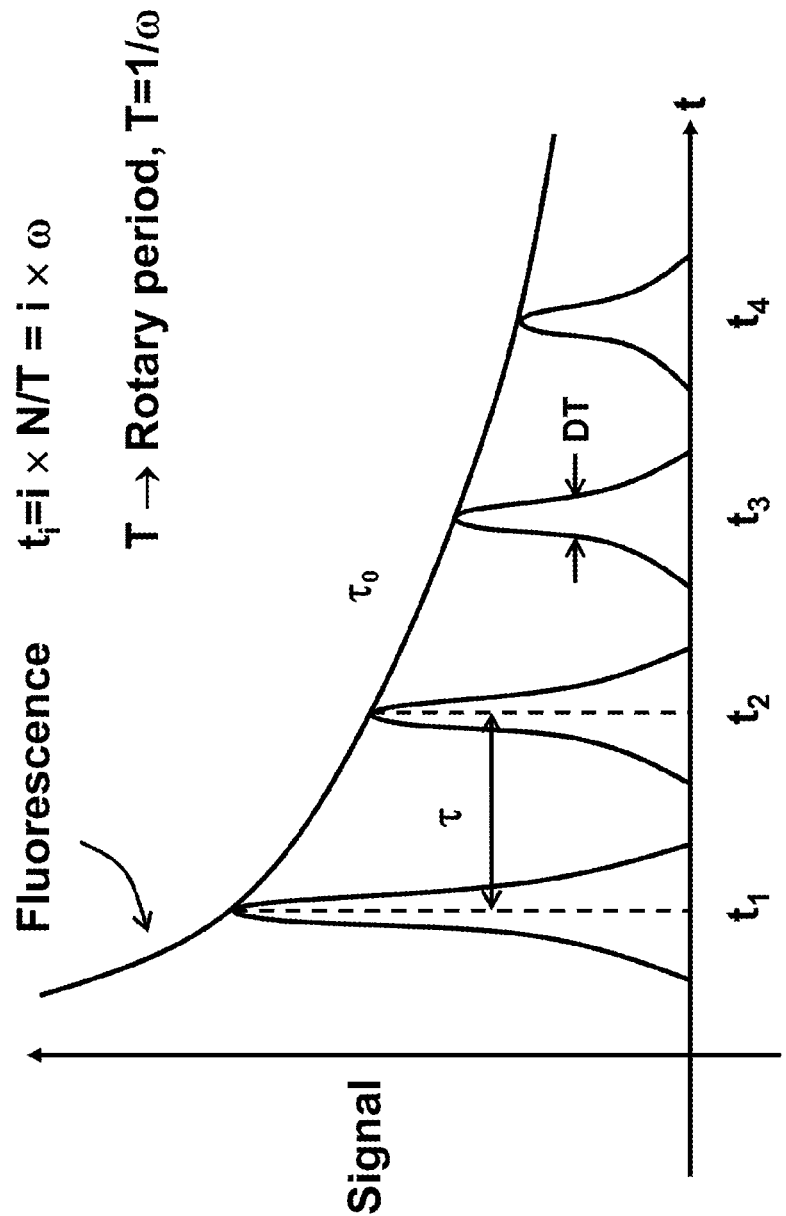
FIG. 2 shows the theoretical time profile of an exponentially decaying optical signal, as measured by the photo-detector from FIGS. 1a and 1b.

FIG. 2 shows the theoretical time-profile of the signal in the instrument, as measured by the photo-detector. The thick, continuous line shows the natural decay of light emission, with lifetime $\tau_0$. The emission is transmitted in discrete time slots by adjacent waveguides 2-1 (corresponding to time slot $t_1$ in FIG. 2) through 2-9 in FIG. 1a of the RadiaLight® switch 50. Each waveguide 2-i transmits a signal occurring at a time, $t_i$, where the index i goes from 1 to N, the number of optical channels or waveguides 2-i in the RadiaLight® switch 50. The time elapsed between each Stokes pulse, $\tau$, depends on the speed, $\omega$, of the time-division multiplexer. The pulse-width of the time slots is the same for each Stokes pulse, as long as the rotational speed, $\omega$, is kept constant. This pulse-width will be referred to as dwell time ($\Delta T$) and depends on the speed, $\omega$, and the geometry of the switch. By increasing the speed of rotation of the prism 5, the time resolution, $\tau$, is reduced accordingly, at the cost of reducing the measurement time, $\Delta T$. In this manner, fluorophores with faster decay times can be analyzed with the instrument.

Figure 3A:
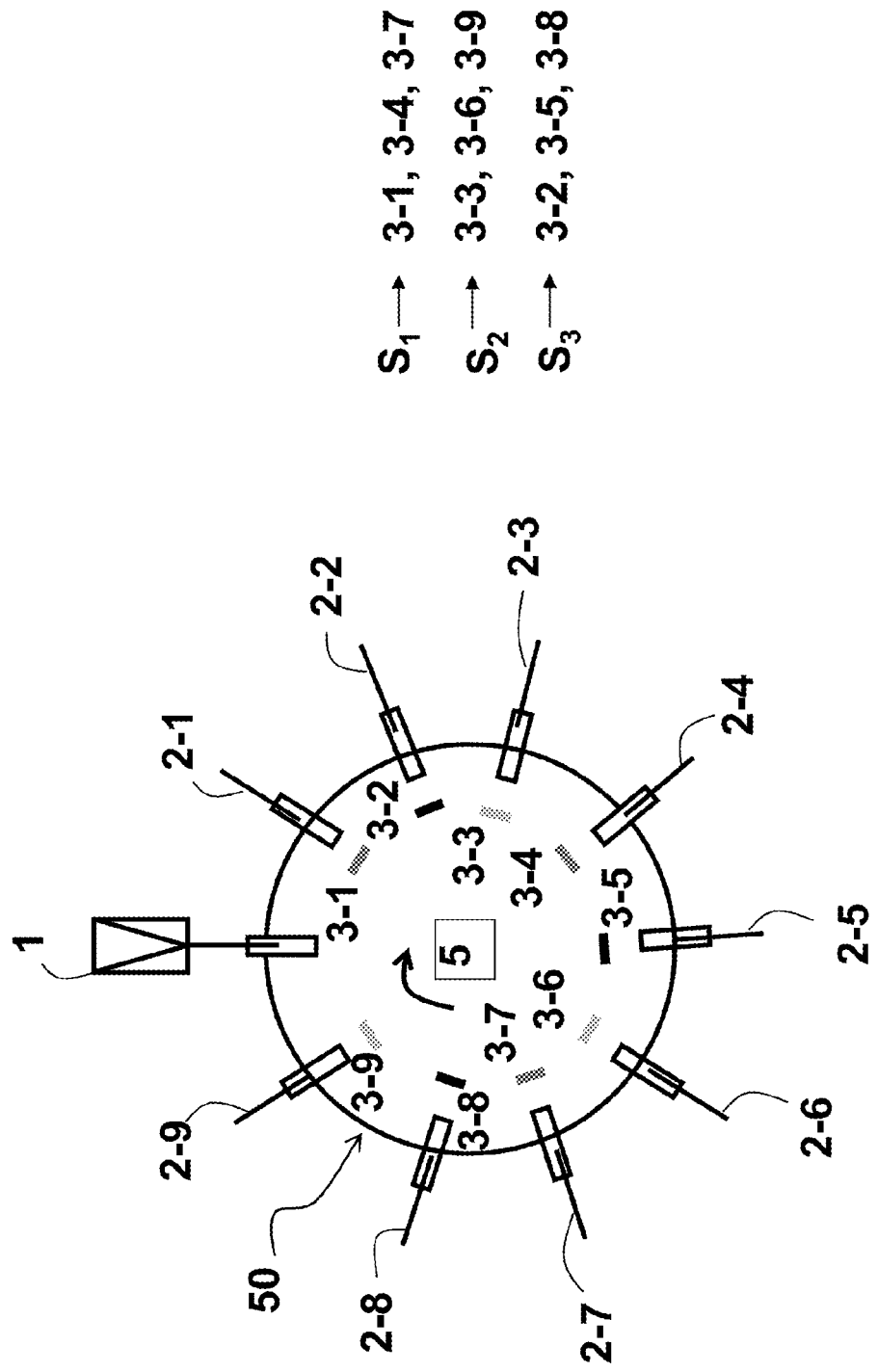

In another embodiment of the invention, illustrated in FIG. 3a, a plurality of optical filters 3-1 through 3-9 is used in the RadiaLight® body 5c in order to distinguish between the Stokes emissions of a plurality of fluorophores placed on the sample 6. FIGS. 3b, 3c and 3d show, respectively, the decay times of three different components $S_1$, $S_2$, and $S_3$ of the sample 6 being analyzed. Notice that reflected light from component $S_1$ is passed by filters 3-1, 3-4 and 3-7 to optical channels 2-1, 2-4 and 2-7, respectively. Reflected light from component $S_2$ is passed by filters 3-3, 3-6, and 3-9 to optical channels 2-3, 2-6 and 2-9, respectively, while reflected light from component $S_3$ is passed by filters 3-2, 3-5, and 3-8 to optical channels 2-2, 2-5, and 2-8, respectively. The time shifts of the reflected fluorescent light pulses shown in FIGS. 3b, 3c, and 3d reflect the times for prism 5 to rotate so as to direct the reflected light to the appropriate optical channels 2-1 to 2-9 in sequence. Filters 3-1 through 3-9 allow only the light from the desired fluorophore to pass into the appropriate optical channel 2-1 through 2-9.

Figure 4A:
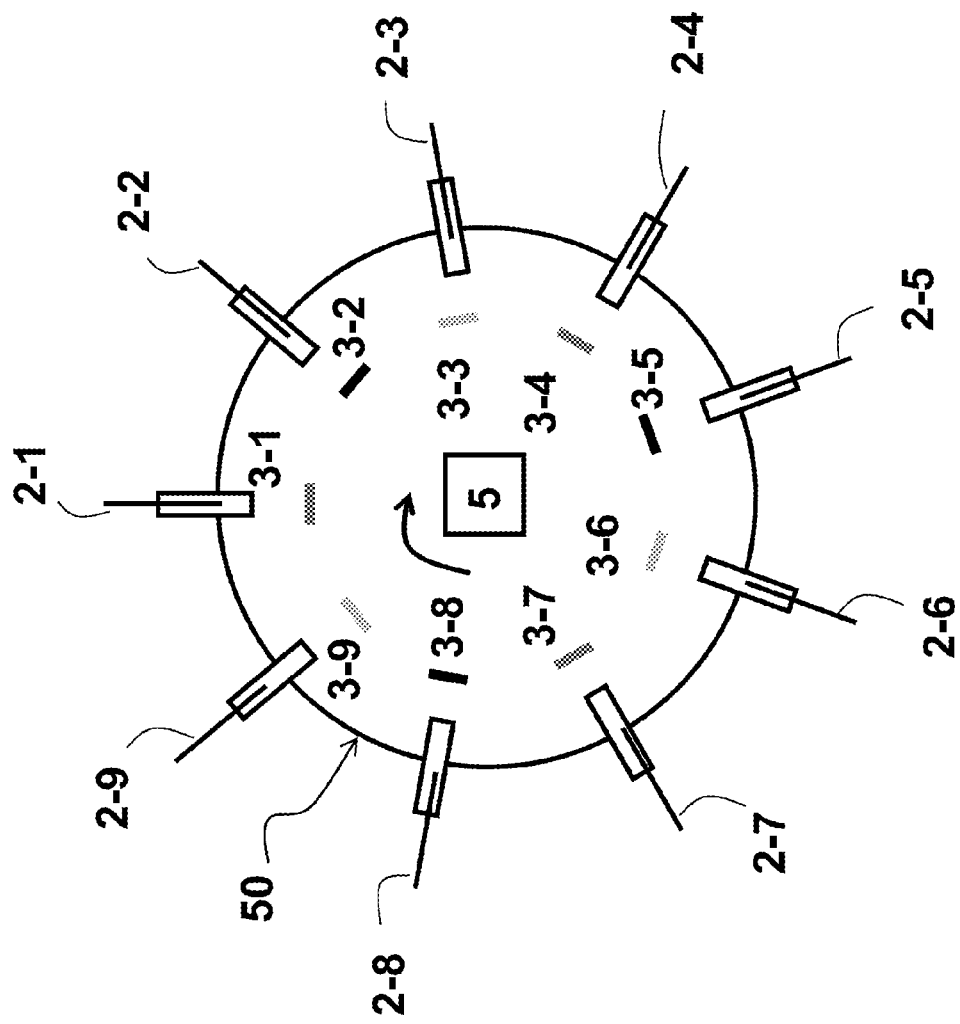
FIGS. 4a and 4b show an embodiment of this invention using a multiplicity of optical filters 3-1 to 3-9 to perform fluorescence correlation spectroscopy (FCS) and fluorescence cross-correlation spectroscopy (FCCS). A blocking filter, 9, is introduced to prevent the pump light reflected off of the sample from going into the detecting device.
Figure 4B:
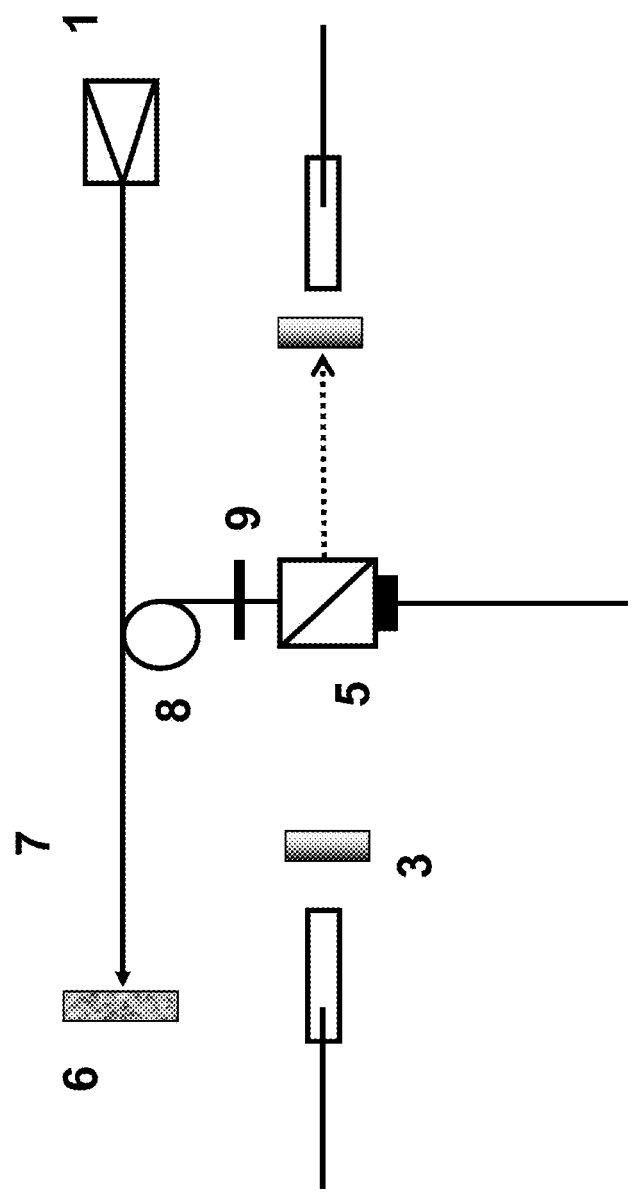

Yet another embodiment of the present invention is illustrated in FIGS. 4a and 4b. Here, a plurality of optical filters 3-1 through 3-9 is also used to distinguish between the light emission of a plurality of compounds. In this case, the signals are produced and collected at different time intervals; the pump optical signal from laser 1 is continuous, and the decay lifetime of the emitting compounds can be as short as a few ns, but no longer than the $\Delta T$ (see FIG. 2 for a definition of $\Delta T$) of the RadiaLight® device 50 at the operational speed. The pump optical signal from laser 1 is transmitted along waveguide 7 to sample 6 and the reflected radiation from sample 6 is passed back along waveguide 7 to routing element 8 and then through an additional filter 9 which blocks the light from laser 1. This configuration enables the use of correlation techniques between different emitters (FCCS), or auto-correlation techniques for each target (FCS). Also note that for this configuration additional filter 9 is needed before or after the routing element 8 (shown in FIG. 4a as after the routing element 8), so as to block all light that contains the frequency of the pump light from going into the RadiaLight® switch device 50 and from there into the waveguide optical channels 2-1 through 2-9.

The algorithms used by the present invention to measure the signal from a sample that is composed of a plurality of emitters that have different decay lifetimes, $\tau_i$, will be disclosed in the following. A person of ordinary skill in the art will recognize that the application of the algorithms can be broader than the uses described herein. In particular, the following algorithms 1 through 4 can be implemented together with any time-resolved instrumentation in order to perform multiple species evaluation of exponentially decaying processes. The first algorithm belongs to a wider set of techniques that in accordance with this invention will be called discrete Principal Component Analysis (dPCA). The first algorithm involves the use of dPCA techniques to evaluate the concentrations of multiple compounds simultaneously in a given sample, each compound having determined and fixed emission lifetime decay, or attached to an emitter that has determined and fixed lifetime decay. The other three algorithms are concerned with the evaluation of both the concentrations and the lifetimes of multiple compounds simultaneously, in a given sample. The second of these algorithms makes use of a dPCA technique supplemented with an auxiliary function (see equation 8). The last two algorithms belong to a set that will be called "discrete Laplace Transform" techniques. One of these two algorithms makes use of a discrete speed scan of the time-resolved spectrometer, and the other uses a continuous speed scan of the time-resolved spectrometer and integration in discrete time-segments of the signal.

Algorithm No. 1.

Notwithstanding the spectral composition of the light emission coming from the different compounds in the sample, the intensity of radiation produced by a number of emitting compounds (say, K), as a function of time, is simply given as the incoherent addition of each individual compound, $$I_F(t) = \sum_i^K \alpha_i \eta_i \chi_i \cdot e^{-t/\tau_i} \quad (1)$$

Where, $\chi_i$, is the concentration of the i-th substance, $\alpha_i$, its absorbance, $\eta_i$, its emission quantum efficiency and, $\tau_i$, its emission lifetime. To arrive at Eq. (1), the limit of small absorbance for the compounds is assumed. Since $\{\alpha_i\}$ and $\{\alpha_i \eta_i\}$ are fixed quantities, we can recombine the three factors in the coefficients of Eq. (1) as a single set of unknowns, $\{\zeta_i\} = \{\alpha_i \eta_i \chi_i\}$. A compound can be an atom, a molecule or a more complex cluster of atoms and molecules. A compound is sometimes called a component. Typically, a sample of material being analyzed will contain a plurality of components or compounds.

In one of the embodiments of the instrument, it will be assumed that the lifetimes, $\{\tau_i\}$, of the compounds are known values which remain constant during the course of the measurement and are only slightly affected by environmental conditions (such as pH, Temperature, viscosity, humidity pressure). In this case, the compound concentration, $\{\chi_i\}$ is being measured, and the time-resolution is understood as the ability of the RadiaLight® based spectrometer system to determine $\{\chi_i\}$ within a time window equal to the roundtrip time of the device. The linearity of Eq. (1), with respect to compound concentrations, $\{\chi_i\}$, allows for the use of linear regression techniques in de-convolving the time-domain signal at the photo-detector level, when a sample composed of a plurality of emitting or absorbing substances is being interrogated. By defining the elements of an N×K matrix, $\sigma$, as $$\sigma_{ij} = \frac{\alpha_j \eta_j}{N \cdot \Delta T} \int_0^T e^{-t/\tau_j} \cdot e^{-(t-t_i)^2/\Delta T^2} dt \quad (2)$$

$i = 1 \ldots N \rightarrow$ number of optical channels;

$j = 1 \ldots k \rightarrow$ number of analytes.

Furthermore, defining a vector, A $(a_1 \ldots a_N)$, where $a_i$ is the integrated optical power received by the photo-detector after polling the i-th optical channel, divided by the dwell time, $\Delta T$ (see FIG. 2), it follows, then $$A = \sigma \cdot \chi \quad (3)$$

Eq. (2) is a convolution of the exponentially decaying function of a light emitting compound with an optical channel transmission function. In some embodiments of the present invention, the optical channel transmission function may be a Gaussian function, as shown in Eq. (2); however, some embodiments may include other optical channel transmission functions, like a Voigt profile, or a Lorentz profile.

Once the photo-detector measurement is expressed in a linear operation as shown in Eq. (3), the algebra of regression techniques can be applied directly in a manner such as disclosed in U.S. Pat. No. 7,602,488, assigned to Neptec Optical Solutions, incorporated herein by reference in its entirety. A new matrix, Z, is defined:

$$Z = \sigma^t \cdot \sigma \quad (4)$$

Z is a square, symmetric matrix, and therefore it can be diagonalized and inverted by a unitary matrix, Q, as in:

$$Z = Q^t \cdot \Lambda \cdot Q \quad (5)$$

where, $\Lambda$, is a diagonal matrix containing the eigenvalues of Z. From Eqs. (3), (4) and (5), a solution can be found for $\chi$ as $$\chi = Q \cdot \Lambda^{-1} \cdot Q^t \cdot \sigma^t \cdot A \quad (6)$$

Figure 5A:
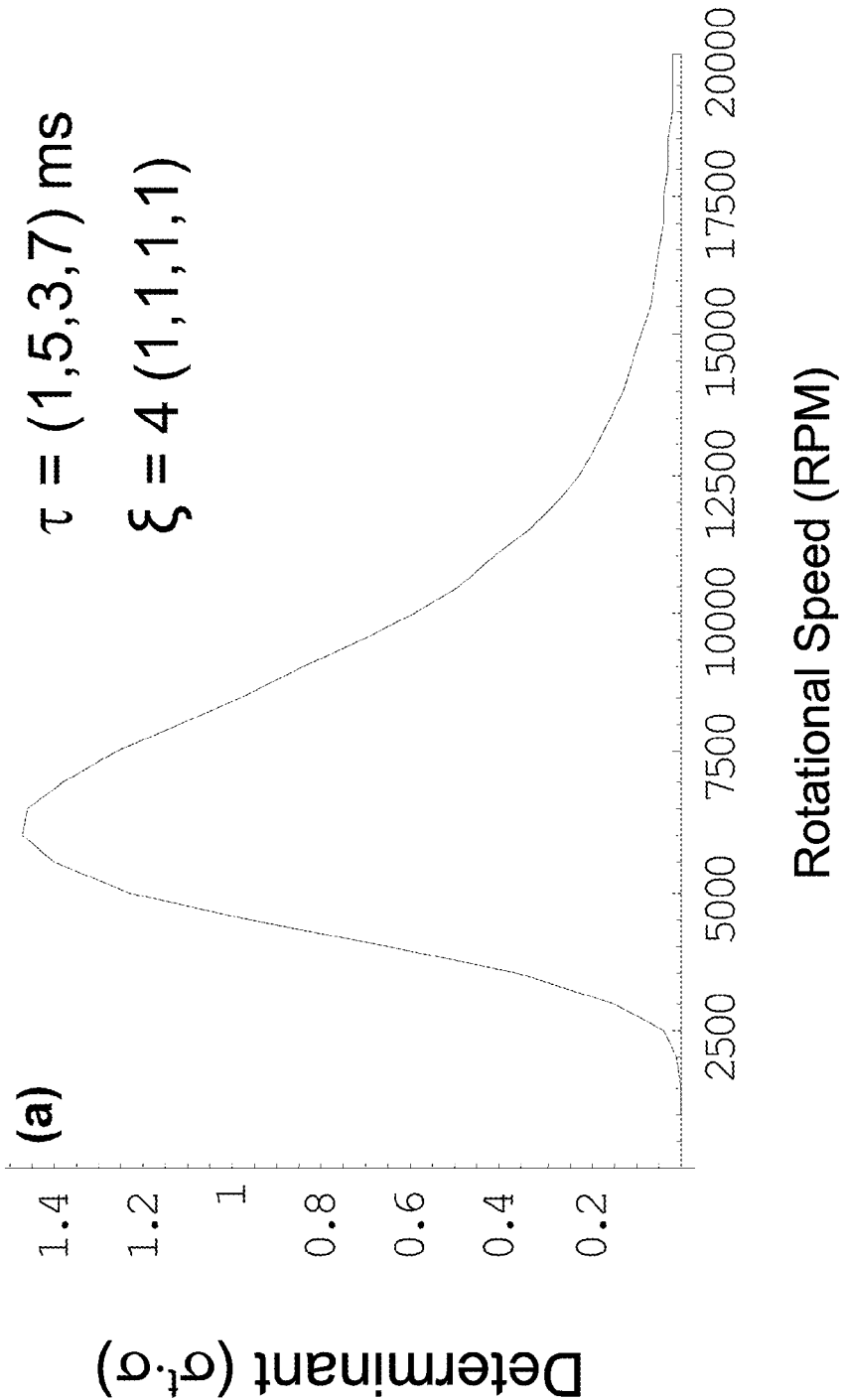
FIGS. 5a and 5b show a determinant, $\gamma$, of the matrix, $\sigma^T \cdot \sigma$, defined in Eq. (2), as a function of rotational speed. A sample containing four different emitting compounds with equal concentrations is illustrated. The time-resolved spectrometer is operated at the speed that maximizes the determinant. (b) The shorter the lifetime of the emission from the compounds, the higher the operational speed of the device needs to be, in order to maximize, $\gamma$.
Figure 5B:
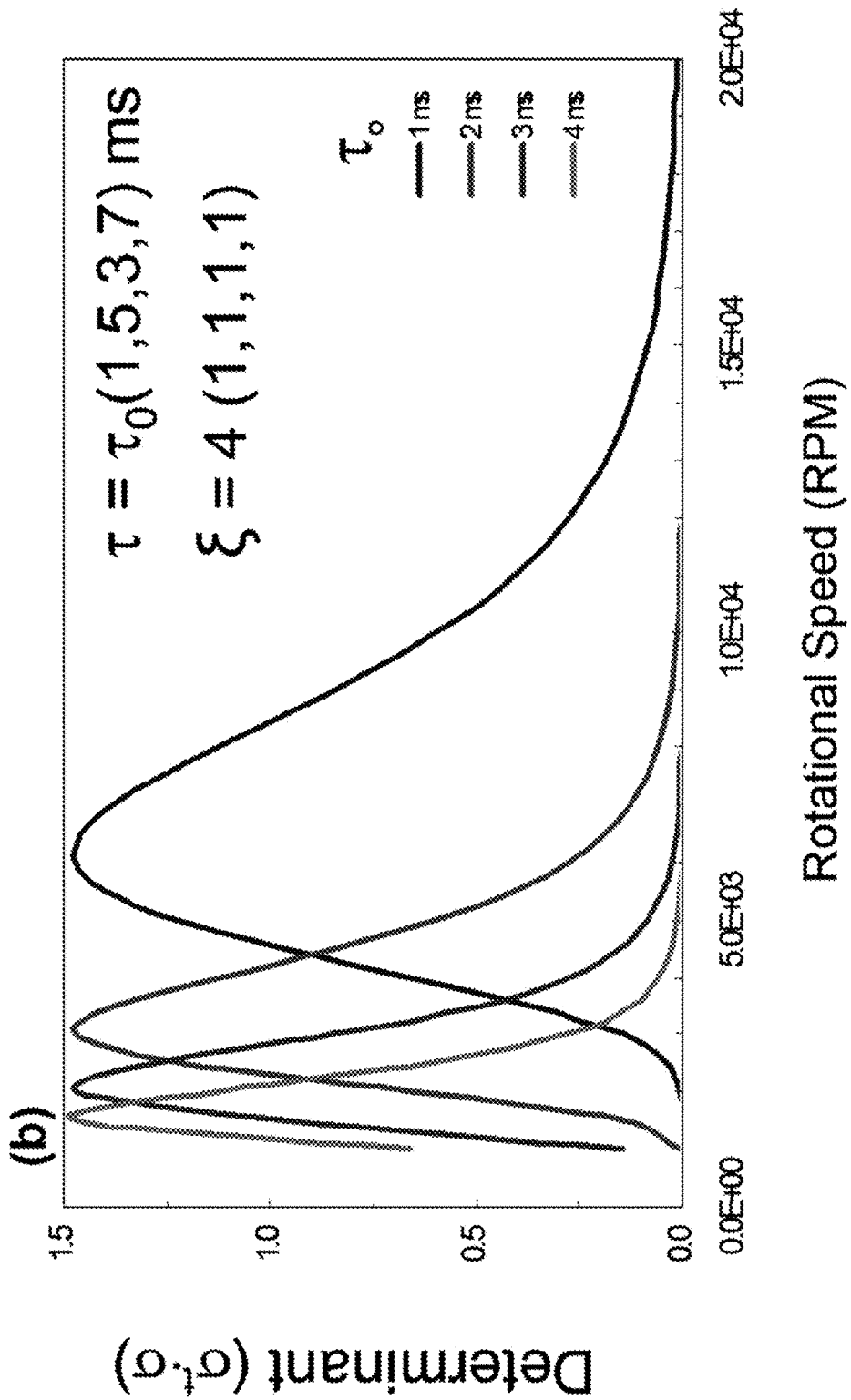

In some embodiments of the present invention, for the matrix inversion to allow for minimal error, and for the algorithm to take the least number of operations, the value of, $\gamma = \text{Det}(Z)$, is maximized. FIG. 5a shows a plot of $\gamma$ as a function of $\omega$ for a given set of $\{\tau_i\}$ and $\{\alpha_i, \eta_i\}$ of a hypothetical sample. The curve has a clear maximum, and a fairly broad range of values of $\omega$ for which $\gamma$ maintains a sizeable value (FWHM). In some embodiments of the present invention, the operational speed of the device, $\omega_{op}$, will be defined as that which maximizes the curve of FIG. 5a for a given set of $\{\alpha_i, \eta_i\}$. FIG. 5b shows a set of different curves $\gamma$, given samples with a different range of lifetimes $\{\tau_i\}$. The maximum value of $\gamma$ remains the same as the set of values $\{\tau_i\}$ changes substantially. This relaxes the computational requirements while the instrument performance is maintained uniform across a large range of lifetime values.

An indicator of device performance according to some embodiments of the present invention is the variance introduced in the concentration measurement due to the linear regression applied. This information is contained in the rows of the matrix: $Z^{-1} \cdot \sigma^t$. The variance $\nu$ is defined as $$\nu = \text{Max}\left[\sum_i (Z^{-1} \cdot \sigma)_{ij}\right]. \quad (7)$$

Figure 6:
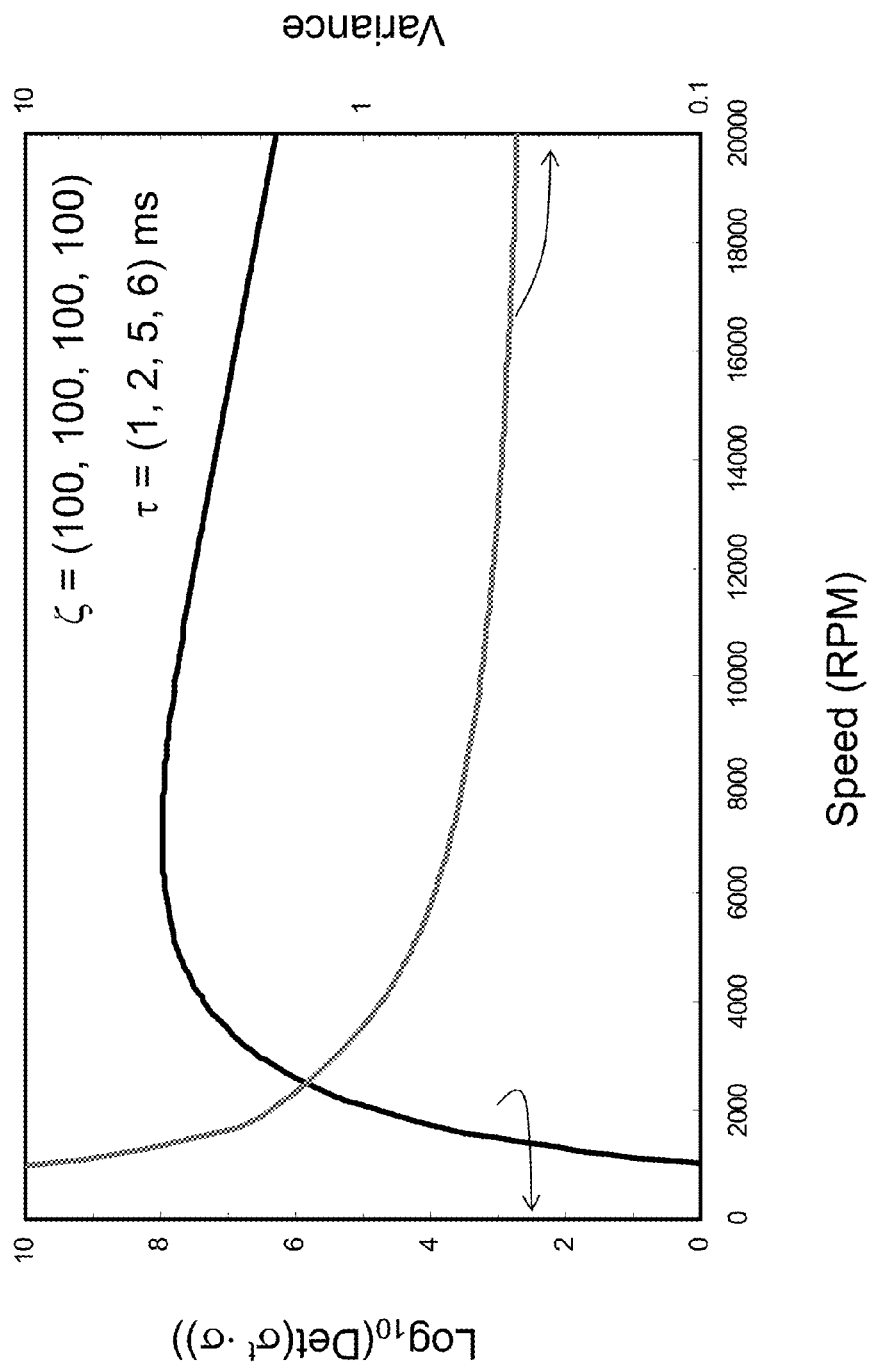
FIG. 6 depicts for the set of $\{\tau_i\}$ and $\{\zeta_i\}$ shown, that the value of $\omega$ which maximizes $\gamma$ (Y-axis on the left) also produces a Variance, $\nu$ (Y-axis on the right), well below 1, as desired.

FIG. 6 shows the relation between $\gamma$ and $\nu$ as functions of $\omega$ using the definition of Eq. (7). It is seen that for the range of values that maximize $\gamma$, the values of $\nu$ are well below 1. This means that the operation of the device is limited only by the photo-detector noise and signal statistics rather than by cross-correlation of data in the multi-species analysis.

Algorithm No. 2.

Using the definition of the variance given in Eq. (7), a further development can be introduced, as described in the following. A reference function $F_R$ can be defined as, $$F_R(t) = I_F(t) + I_{ref} e^{-t/\tau_{ref}}. \quad (8.1)$$

where $I_F$ is given by Eq. (1), $\tau_{ref}$ is a reference lifetime, and $I_{ref}$ is a reference amplitude. With the function $F_R$ a matrix, $\sigma(I_{ref}, \tau_{ref})$, is built and the variance $\nu(I_{ref}, \tau_{ref})$, is calculated following Eqs. (7-8.1), as shown below, $$\sigma_{ij}(I_R, \tau_R) = \frac{1}{N \cdot \Delta T} \int_0^T (\alpha_j \cdot \eta_j \cdot e^{-t/\tau_j} + I_R \cdot e^{-t/\tau_R}) \cdot e^{-(t-t_i)^2/\Delta T^2} dt. \quad (8.2)$$

Figure 7:
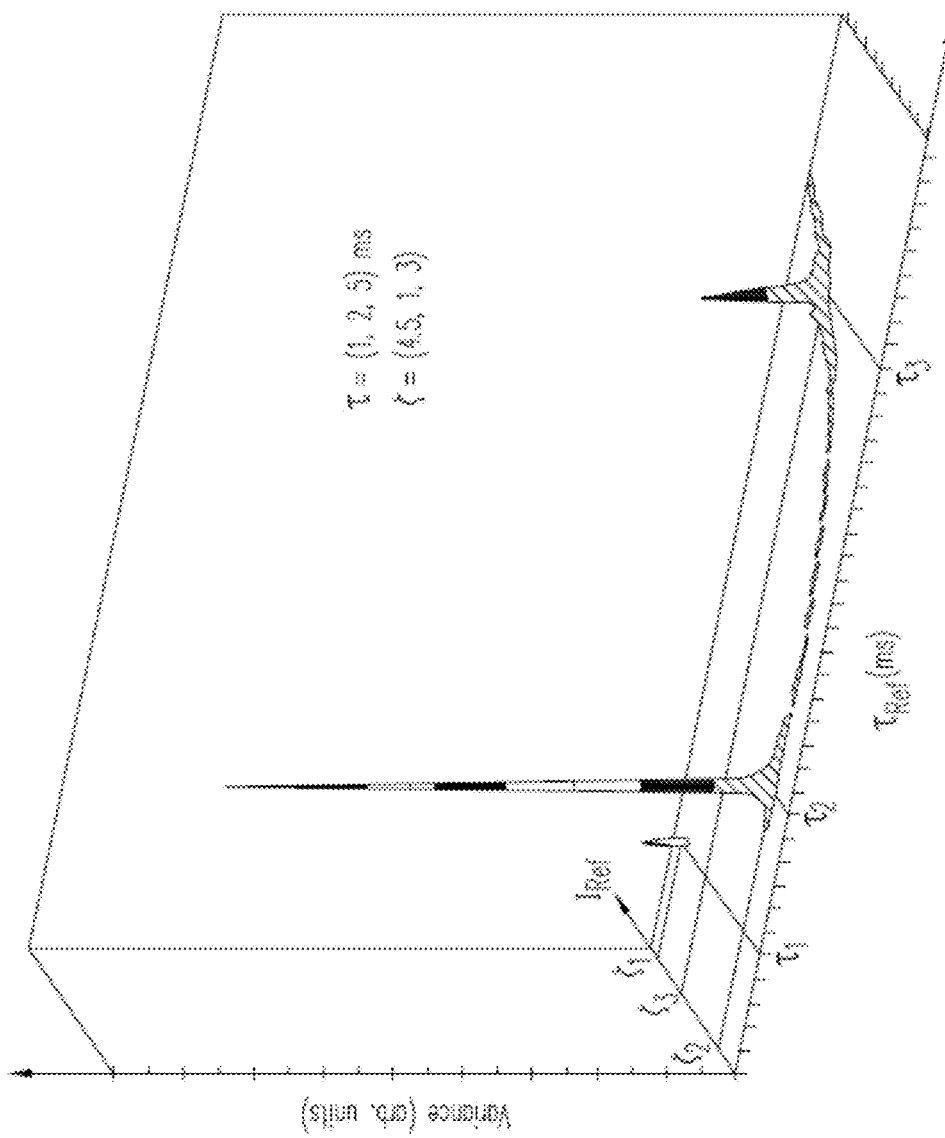
FIG. 7 shows a plot of the variance (Eq. 7) of the signal in the device of FIGS. 1a and 1b as a function of the reference lifetime $\tau_R$, and reference amplitude $I_R$ described in (Eq. 8). A smoothening residual has been added by hand, to avoid the poles of the function. In practice, the inherent dark signals at the photo-detector level will prevent the system from being indeterminate and act as a smoothening function. The net result is a surface that shows clear spikes at values of $\tau_R$ and $I_R$ that match the values of the sets: $\{\tau_i\}$ and $\{\zeta_i\}$. The RadiaLight® device simulated has 25 optical channels (1 mm diameter collimators), and a rotational speed $\omega=7100$ (RPM). At this speed, the sensitivity is maximal for the lifetime range considered (see FIG. 6).

FIG. 7 shows the surface $\nu(I_{ref}, \tau_{ref})$ for $\tau_{ref}$ ranging from 0 to Max $\{\tau_i\}$, and $I_{Ref}$ ranging from 0 to Max $\{\zeta_i\}$, according to one embodiment of the present invention comprising a sample with three compounds having unknown concentrations and unknown emission decay lifetimes. It is shown that $\nu(I_{ref}, \tau_{ref})$ has distinct poles at the points, $\{\tau_i, \zeta_i\}$. An operation that produces a function as described in Eq. (8.1) can be carried out electronically, at the level of the amplifier circuit, or optically, by use of a reference signal of some sort.

Algorithm No. 3.

Figure 8:
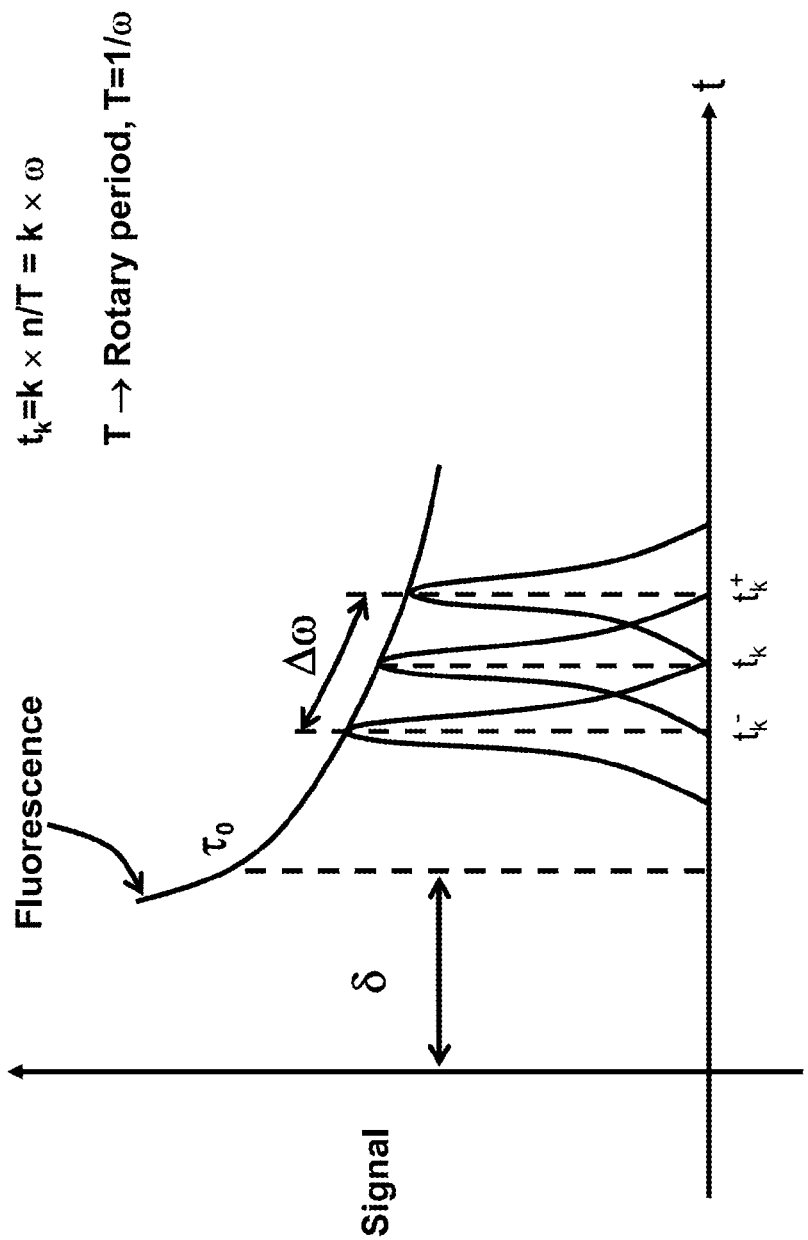
FIG. 8 shows the theoretical time-profile of the optical signal in a single optical channel of the device, as it would appear when performing the step-speed-scan algorithm for lifetime measurements.

Another embodiment of the instrument comprises a discrete Laplace transform algorithm, used to measure the different lifetimes and concentrations, $\{\tau_i\}$ and $\{\zeta_i\}$ in Eq. (1). This algorithm is illustrated in FIG. 8. The method of using a Laplace transform to solve Eq. (1) in terms of $\{\chi_i\}$ and $\{\tau_i\}$ has been well-known for a number of years (See M. Ameloot, J. M. Beechem, L. Brand; "Simultaneous Analysis of Multiple Fluorescence Decay Curves By Laplace Transforms", Biophysical Chemistry 23, 155171 (1986)). Equations (9.1-3) in U.S. patent application Ser. No. 11/603,939 show the three discrete functions that will be of relevance.

Eq. (9.1) in U.S. patent application Ser. No. 11/603,939 is proportional to the intensity measured by the k-th optical channel of the RadiaLight® switch, and Eqs. (9.2) and (9.3) in U.S. patent application Ser. No. 11/603,939 are its successive time derivatives. Throughout this discussion, a sample with three different species will be used for calculations and examples. A person of ordinary skill in the art will recognize that the technique can be extended to a sample with any number K of components. FIG. 8 shows the basic principle for the step-speed scan technique. In FIG. 8, a single optical channel signal is shown for different values of the rotational speed $\omega$ of the device. Here, the device is operated at a central speed $\omega_0$ for one complete cycle. The speed is then increased to a value $\omega^-$, and a new set of measurements is collected through another cycle. The choice of '−' superscript is based on the fact that, whereas, $\omega^+ < \omega_0 < \omega^-$, also, $t_k^- < t_k < t_k^+$. This is followed by a new cycle scan measurement, where the speed of the device is reduced to $\omega^-$. With the measurements performed in this manner, the first and second time derivatives of the intensity can be collected for every optical channel in the device, as shown in Eq. (10) of U.S. patent application Ser. No. 11/603,939, incorporated herein by reference in its entirety.

On the other hand, the optical power intensity I(t), measured by the photo-detector as the RadiaLight® switch cycles through the optical channels, is a function of time to which a Laplace transform can be applied, with the result written in Eq. (11) of U.S. patent application Ser. No. 11/603,939, incorporated herein by reference in its entirety.

The right hand side in Eq. (11) of U.S. patent application Ser. No. 11/603,939, includes a sum of terms that can be obtained by direct, discrete measurement with the RadiaLight® device, using the supplementary functions of the parameter s, shown above. These functions include factors that involve knowledge of $t_k$ at every point of the measurement, which is also a design parameter in the RadiaLight® architecture. The functions $I_k'$ and $I_k''$ can also be obtained from measurement, as shown in FIG. 8, and Eq. (10) in U.S. patent application Ser. No. 11/603,939; in this case, knowledge of $t_k$ is necessary at three different points for each optical channel k and measurements at three different values of $\omega$ are also needed. Overall, evaluation of the right-hand side of Eq. (11) in U.S. patent application Ser. No. 11/603,939, requires measurement of $I_k$ at three different speeds, and the collection of ($\omega$, $\omega^+$, and $\omega^-$), and ($t_k$, $t_k^+$, $t_k^-$). This means that, for each measurement, at least three complete cycles of the RadiaLight® switch will be needed, for a total of 3 k+6 parameters. Furthermore, in some embodiments of the present invention the number of cycles needed to complete a measurement may be larger. A calculation of the Laplace transform of a continuous emission or transmission decay function renders Eq. (12) in U.S. patent application Ser. No. 11/603,939, incorporated herein by reference in its entirety.

Eq. (12) in U.S. patent application Ser. No. 11/603,939, is a rational function of polynomials, with parameters, $\{\zeta_i\}$, and, $\{\tau_i\}$. These functions are readily suitable for nonlinear curve fitting by any standard method available, e.g. Levenberg-Marquardt routines. The procedure is to equate the right hand side of Eq. (12) in U.S. patent application Ser. No. 11/603,939 to the right hand side of Eq. (11) in U.S. patent application Ser. No. 11/603,939. Some embodiments of the present invention employ a nonlinear curve fitting to the data in the right hand side of Eq. (11) in U.S. patent application Ser. No. 11/603,939, in order to extract the parameters $\{\zeta_i\}$ and $\{\tau_i\}$ altogether. In some embodiments of the present invention, time-division multiplexer 50 creates a time-gap, $\delta$, between the optical pumping and the start of the measurement, as shown in FIG. 8. In some embodiments, the RadiaLight® device operates such that $\delta = t_1$; however, other embodiments may use $\delta$ as an independent parameter that can be adjusted by special design of the instrument. The issue will be to select values of $\delta$ that are convenient so that the model can accurately predict $\{\zeta_i\}$ and $\{\tau_i\}$ for a given sample. The starting point is to replace the integral in Eq. (12) from U.S. patent application Ser. No. 11/603,939 by a modified Laplace transform $L_s^{\delta}(I)$ as shown in Eq. (13) of U.S. patent application Ser. No. 11/603,939.

Figure 9:
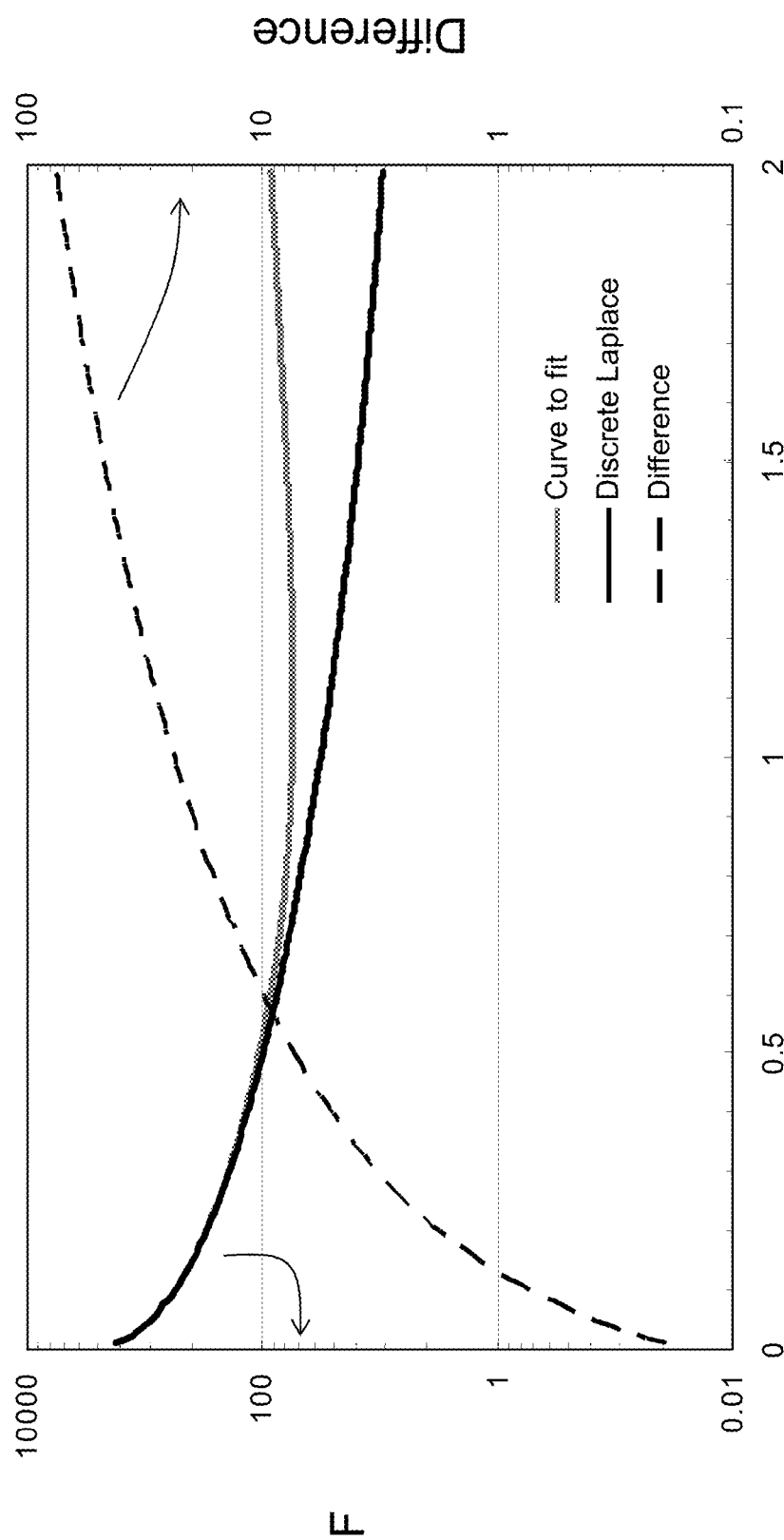
FIG. 9 shows the difference between curve to fit (Eq. (14), left-hand side), and discrete Laplace Transform (Eq. (14), right hand side), using a RadiaLight® TRF spectrometer with 100 optical channels, $\omega=5\times10^5$ (RPM). S is the Laplace parameter. The sample considered has $\{\zeta\}=(10, 30, 70)$, and $\{\tau\}=(30, 50, 10)$ µsec.

The assumption of some embodiments of the present invention is expressed in Eq. (14) of U.S. patent application Ser. No. 11/603,939. The validity of Eq. (14) in U.S. patent application Ser. No. 11/603,939 occurs for only a given range of values of s. FIG. 9 shows a plot of the two sides of Eq. (14) in U.S. patent application Ser. No. 11/603,939, for $\delta = \tau = 1.2$ µsec. In some embodiments of the method presented here the nonlinear fit is performed in a region for small s, so that the equality of the two sides of the equation is maintained with sufficiently good precision. Also, notice that the left-hand side of Eq. (14) in U.S. patent application Ser. No. 11/603,939 is obtained assuming integration over an infinite time interval. What this means is that the longer the RadiaLight® device polls the signal optical channels after a given pump pulse, the more accurate the equation will be. Therefore, multiple measurement cycles may be needed after a pump pulse is delivered. This is in addition to the three cycles at different speeds that the discrete scheme requires, in order to obtain a measurement.

Figure 10:
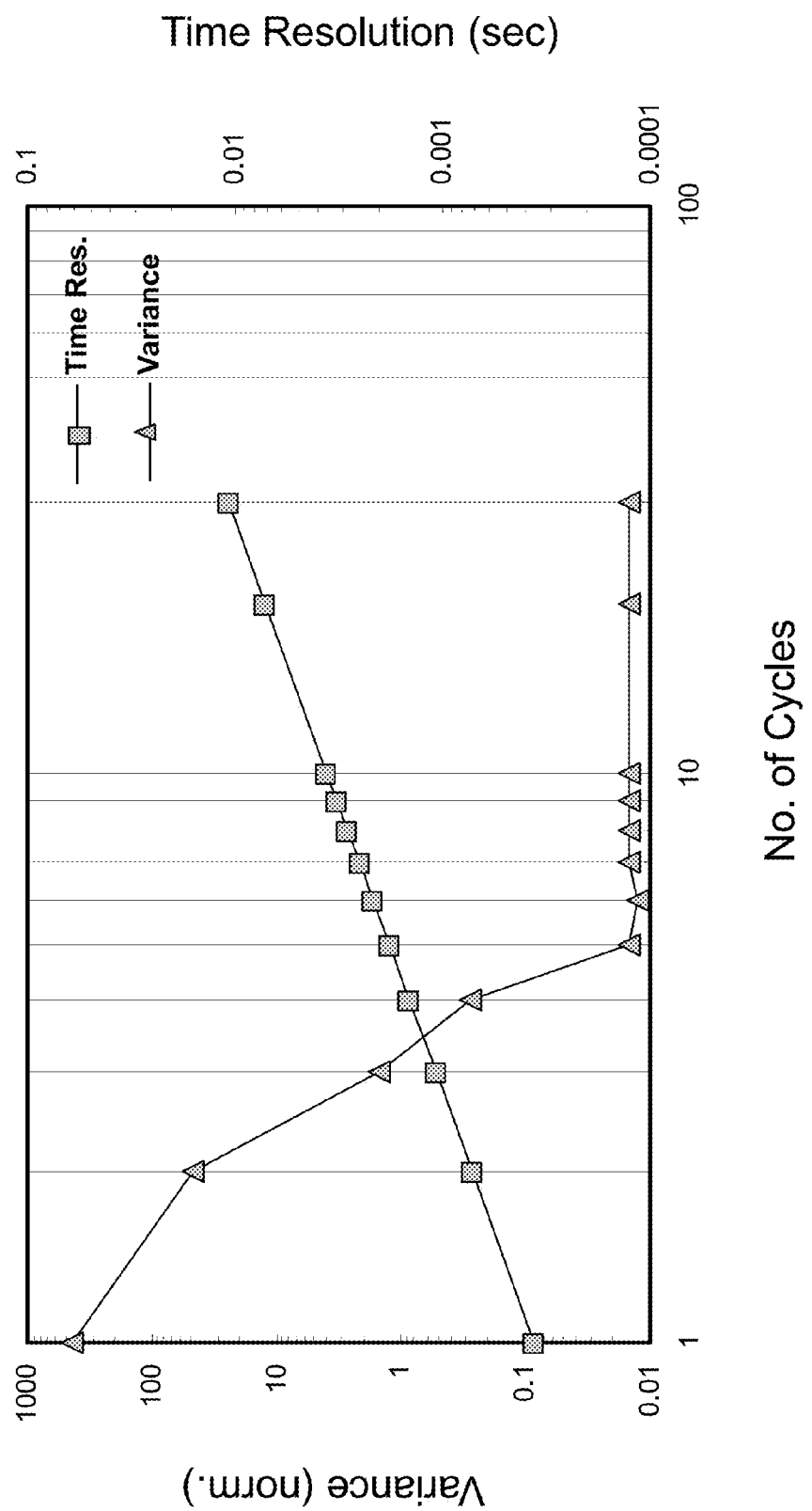
FIG. 10 plots variance and time resolution as a function of the number of cycles per measurement. The values of $\{\overline{\zeta}_m\}$, $\{\overline{\tau}_m\}$, and $\omega$, are as in FIG. 9, above. Note that even for 30 cycles, the overall time resolution is well below 100 ms.
Figure 11:
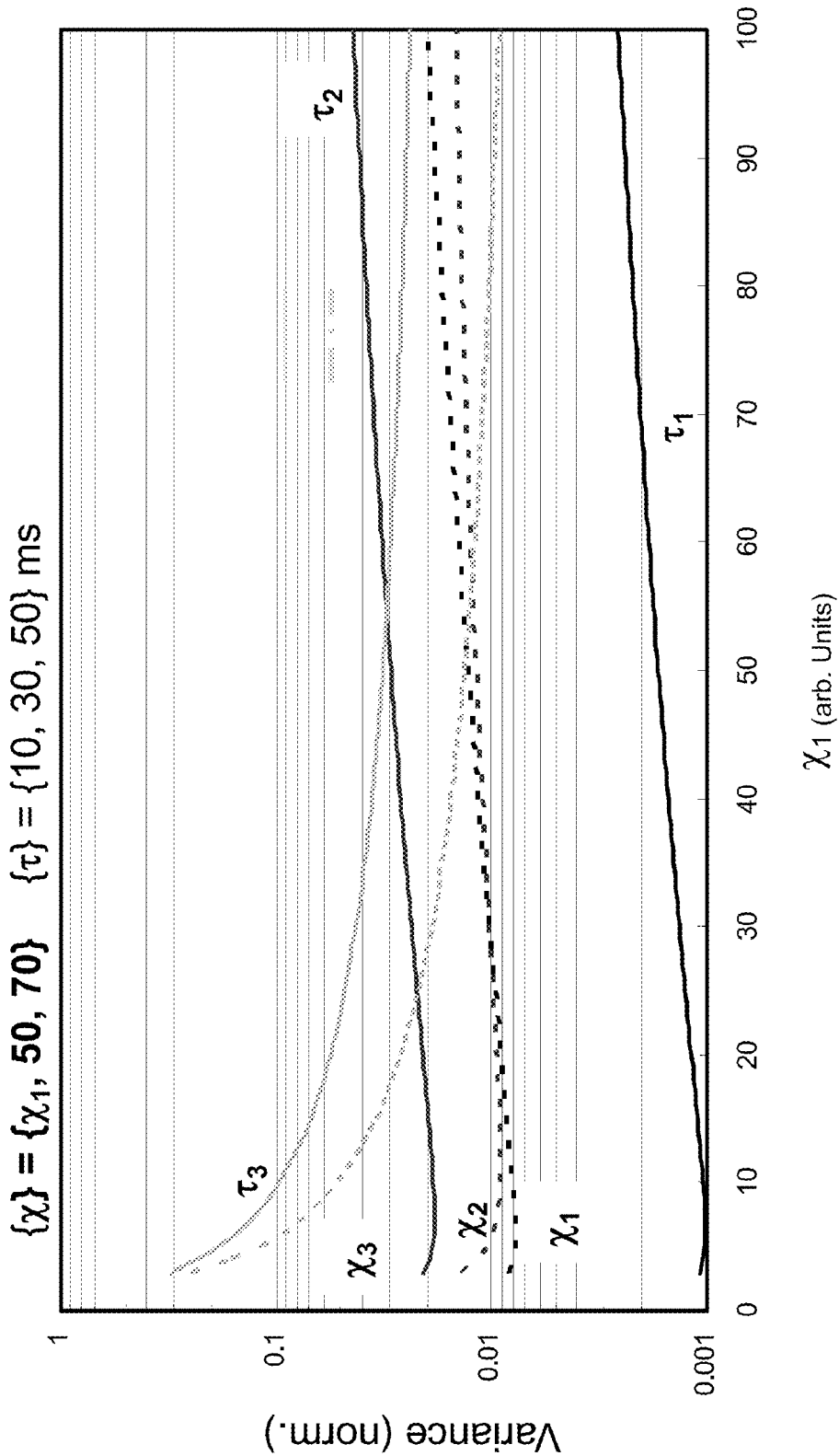
FIG. 11 shows the variance of all six parameters, $\{\overline{\zeta}_m\}$, $\{\overline{\tau}_m\}$, as the concentration $\zeta_1$ of compound 1 is varied. Most of the values lie in the 2-4% variance range.

For a quantitative analysis, some embodiments of the present invention may use a variance of the measurement, or goodness of fit, $\nu$, as in Eq. (15) of U.S. patent application Ser. No. 11/603,939. FIG. 9 shows how sensitive the value of $\nu$ is with respect to the number of cycles in a measurement. Once the low-variance limit is reached, any further increase in cycling will no longer produce better results. The precise value at which this condition is met depends strongly on the specific values of the true parameters $\{\zeta_m\}$ and $\{\tau_m\}$ in Eq. (15) of U.S. patent application Ser. No. 11/603,939. FIG. 10 also shows the time resolution of the measurement for the different cycles used, including a factor of 3, to account for the step-speed scan. For the center speed used in the calculation ($\omega = 5 \times 10^5$ RPM), it is seen that cycling the instrument up to 30 times per measurement results in a time resolution of about 10 ms. FIG. 11 shows the correlation of the variances between the different parameters, as the concentration of compound 1 changes. Correlation is high, but variances are kept below 5% across a wide range of values for $\zeta_1$.

Algorithm No. 4.

Figure 12A:
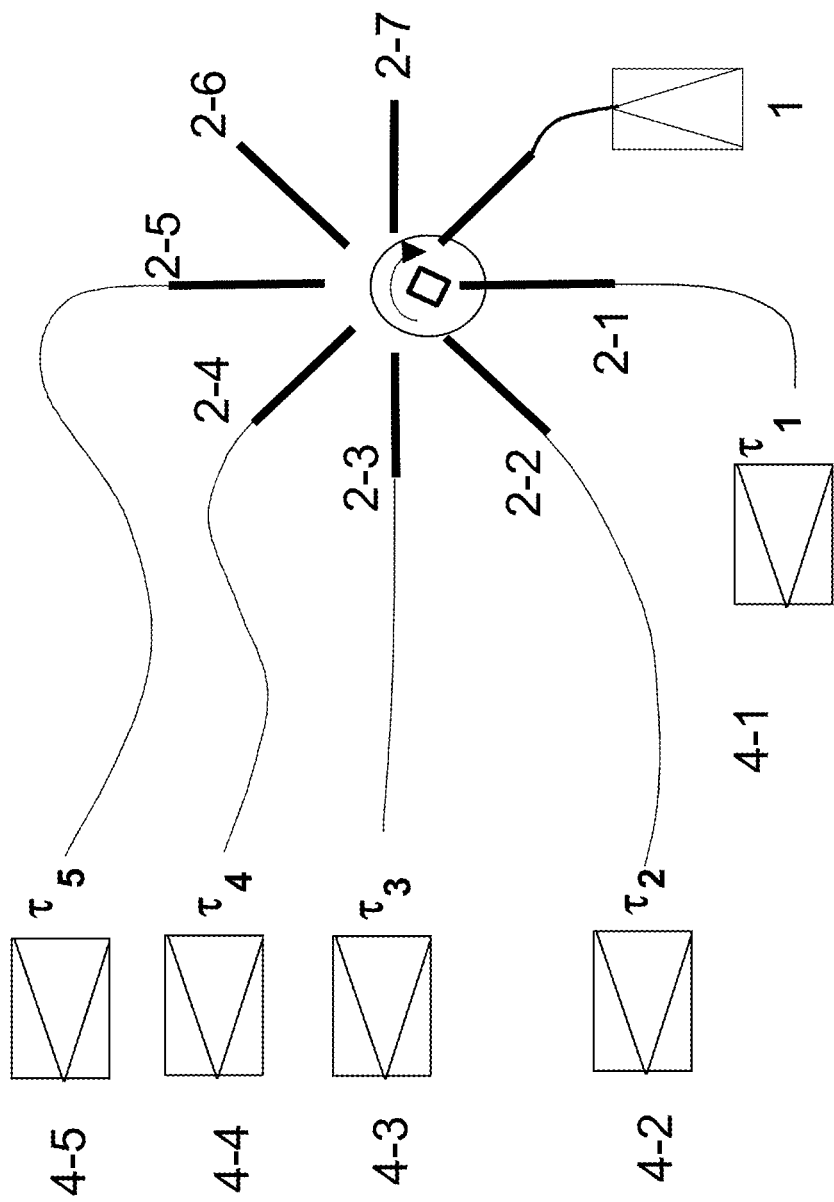
FIG. 12a shows a system using separate photo-detectors 4-1 to 4-7 (photo-detectors 4-6 and 4-7 are not showing) for each optical channel 2-1 to 2-7 shown to perform a continuous speed-scan measurement of a time-resolved emission spectrum. Notice that, in this configuration, each optical channel in the RadiaLight® device uses a different photo-detector 4-i. Elements in FIG. 12a are numbered the same as corresponding elements in the system of FIGS. 1a and 1b.
Figure 12B:
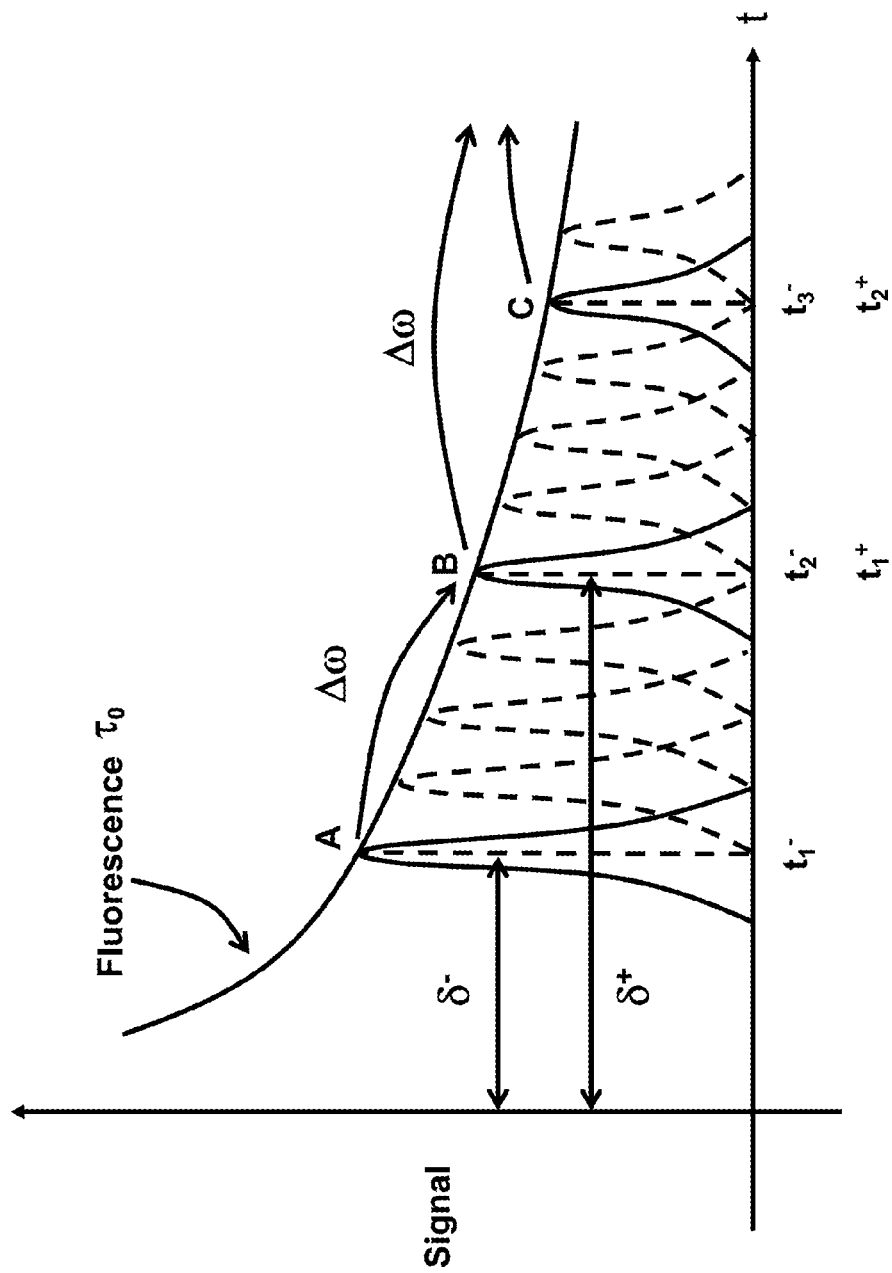
FIG. 12b shows the theoretical time-profile of the emission signal in three different optical channels of the device. The measurement configuration of the device shown in FIGS. 1a and 1b corresponds to the continuous speed scan algorithm Number 4 described herein for emission lifetime and concentration measurements.

In some embodiments of the modified Laplace transform algorithm, a continuous speed scan method is applied. A system for implementing this embodiment is illustrated in FIG. 12a and the waveform resulting from the use of the system of FIG. 12a is shown in FIG. 12b. The concept in this case is to continuously change the speed of time division multiplexing device 50 between two limiting values, $\omega^+ < \omega^-$, while the power measured on each optical channel is monitored separately. FIG. 12a shows the system used for the measurement. Shown in FIG. 12a is a rotating prism 5 with seven waveguides 2-1 through 2-7. Laser 1 provides a source of light to be incident on the sample (not shown in FIG. 12a but located relative to the system in FIG. 12a as shown in FIGS. 1a and 1b). Notice that in the case of a continuous reduction of rotational speed, as the signal from any given optical channel slows down, the device may end up measuring a portion of the signal that had already been measured by a previous optical channel at an earlier time. As a result, different optical channels will end up polling overlapping regions of the time-decay fluorescence signal. This is illustrated in FIG. 12b. Because this could lead to confusion of the overall signal, each optical channel has to be monitored on a separate photo-detector 4-1 through 4-7 of which only photo-detectors 4-1 through 4-5 are shown.

Figure 13:
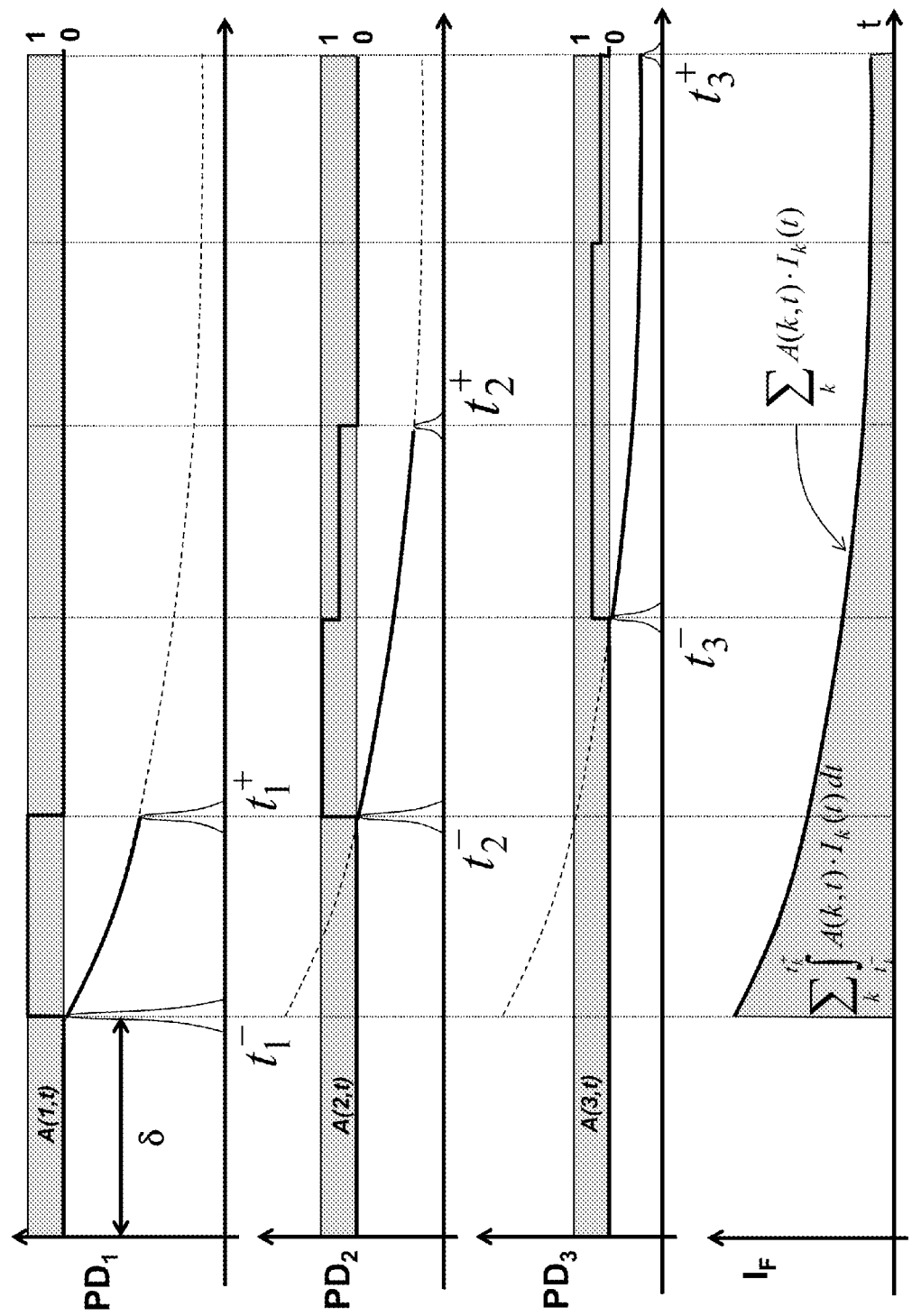
FIG. 13 shows schematically the time-profile measurements of each photo-detector from different optical channels in the RadiaLight® spectrometer, and how they result in the continuous speed scan technique to apply a Laplace transform algorithm. Note also the functions A(k, t), which take into account the overlapping in time of the different signals.

One of ordinary skill in the art will recognize that other embodiments of the invention can be implemented by which the signal from each optical channel is tracked and stored separately by some other electronic means. The process of computing the Laplace transform using the signal coming from each photo-detector and ad-hoc overlap-counting functions, A(k, t), is illustrated in more detail in FIG. 13. In the embodiment illustrated in FIG. 13 the initial and final time-division multiplexing speed of the instrument are such that the first optical channel winds up at the time slot that the second optical channel occupied in the initial configuration. The end result of this process is that a continuous Laplace transform applied to the function $I_F(t)$, starting at an initial time, $\delta \neq 0$, as will be disclosed below. From FIG. 13:

$$I_F(t) = \sum_k A(k, t) \cdot I_k(t)$$

Eq. (16) of U.S. patent application Ser. No. 11/603,939 shows the calculation procedure to find the coefficients $\{\zeta\}$, and $\{\tau\}$. The right hand side is the result of the measurement, where the coefficient A(k,t) takes care of the overlap between the integrals for the different optical channels. This overlap factor depends on the optical channel number, and also on the specific time interval considered. The left-hand side contains the formula and the parameters upon which the nonlinear regression is applied.

In practice, the overlap renders an averaged value of the signal during a certain time interval; this improves the signal-to-noise ratio (SNR) of the device. Once the range of speeds and the number of optical channels is known ($\omega^+$, $\omega^-$, and k), the coefficients A(k, t) can be easily determined. An example is the case illustrated in FIG. 12b. The speeds, $\omega^+$, and, $\omega^-$, are such that the first optical channel ends up being polled at time, $t_1^+ = t_2^-$, so that the overlap between optical channels 1 and 2 is exactly zero. For a simple case with k=8 optical channels in the RadiaLight® switch, the values of the A(k,t) coefficients are listed in Table 1 of U.S. patent application Ser. No. 11/603,939, incorporated herein by reference in its entirety. Notice that the sum across each row is equal to 1, to ensure that the decay measurement during any given time-interval is only counted once.

Figure 14:
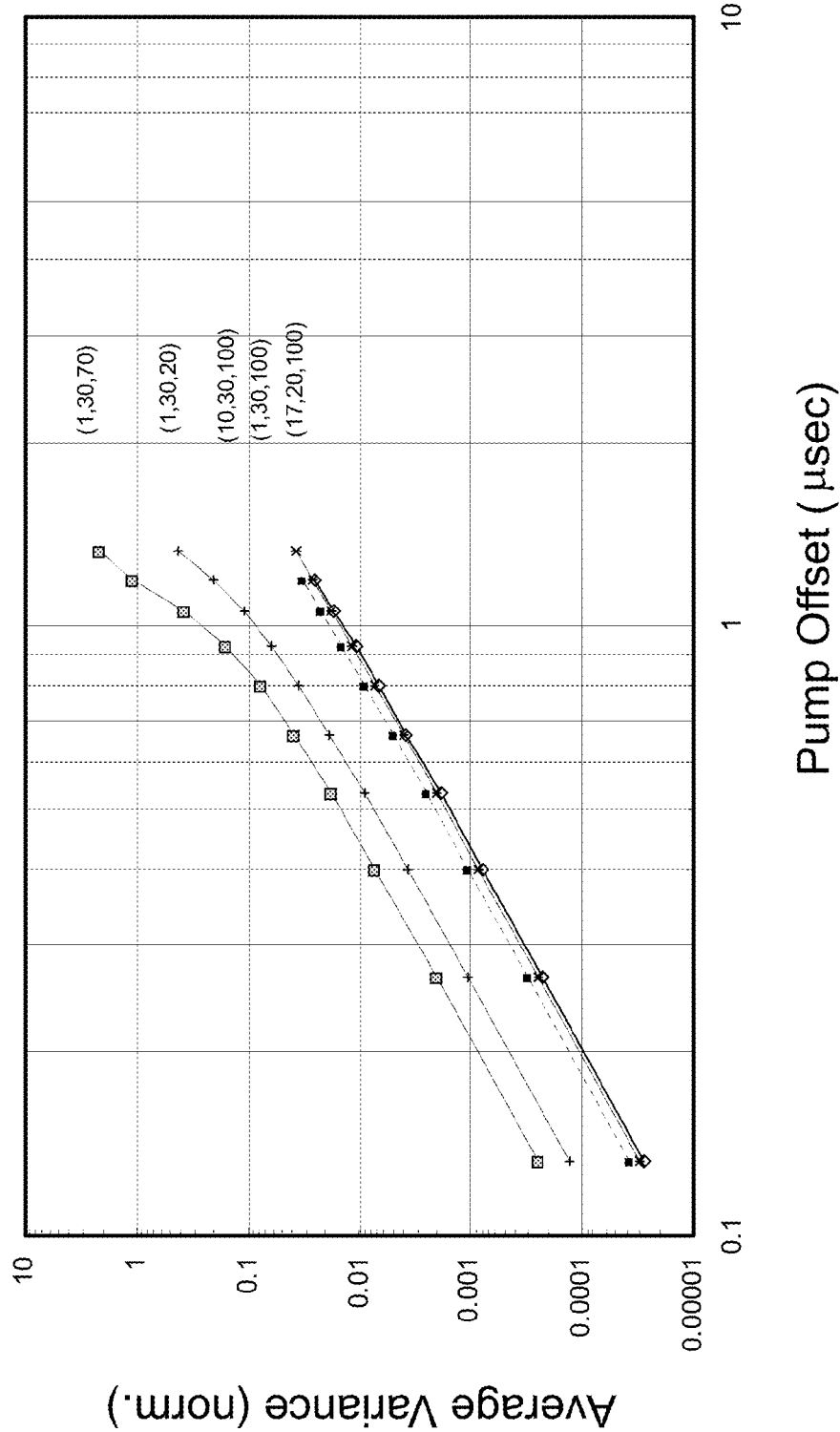
FIG. 14 shows the average variance resulting from a continuous speed-scan algorithm (Eq. 16). The variance is calculated using Eq. (15), and the variable parameter is the pump offset, δ (see FIG. 11). The samples simulated for each curve contain different sets of concentrations, $\{\zeta_i\}$, and $\{\tau_i\}=\{10, 60, 100\}$µs.

FIG. 14 shows the result of a simulation following the procedure outlined in Eq. (16) of U.S. patent application Ser. No. 11/603,939, for different sets of $\{\zeta_i\}$, and $\{\tau_i\} = \{10, 60, 100\}$ µs. The variance is calculated as in Eq. (15) of U.S. patent application Ser. No. 11/603,939, and the variable parameter is the pump offset $\delta$.

The invention disclosed herein can be used in a number of applications. One example is the well known technique of cavity ring-down absorption spectroscopy, also known as cavity ring-down spectroscopy (CRDS). In CRDS, an optical system is so designed to produce a time decaying signal where the decay time has a contribution from the resonant absorption of light at certain frequency due to the presence of a compound in the sample. The total optical intensity as a function of time is a combination of the signal at different frequencies, $\omega_i$, in a manner that parallels Eq. (1):

$$I(t) = \sum_i I_0(\omega_i) \cdot e^{-t/\tau_{\omega i}} \qquad (9)$$

Wherein $\tau_{\omega i}$ has two main contributions:

$$1/\tau_{\omega i} = 1/\tau_i + 1/\tau_{\alpha i} \qquad (10)$$

With $1/\tau_{\alpha i}$ being the contribution from the molecular absorption. The magnitude of $1/\tau_{\alpha i}$ is directly proportional to the concentration of the absorbing molecule in the sample. The factor $1/\tau_i$ is related to "roundtrip" losses in the optical system associated with the elements contained in the system (e.g. mirrors and reflective surfaces, diffraction elements, lenses, waveguide coupling devices). The value of $1/\tau_i$, which in general is dependent on the frequency of light, can be calculated from the physical construction of the optical system. The value of $1/\tau_{\omega i}$ can be obtained from the measurement of the decay times in Eq. (9) using any of the four different algorithms disclosed heretofore, in conjunction with the time-division multiplexer. Thus, a concentration measurement can be directly extracted from the expression $$1/\tau_{\alpha i} = 1/\tau_{\omega i} - 1/\tau_i \qquad (11)$$

By assuming a Beer-Lambert law of absorption for a given molecule over a certain path-length, l, the molecular concentration, $\chi$, is given by:

$$\chi \cdot \alpha = \frac{n}{lc}(1/\tau_{\omega i} - 1/\tau_i) \qquad (12)$$

Wherein $\chi \cdot \alpha$ is the net molecular absorption per unit length of the CRDS system. In one embodiment of the invention disclosed herein, the decay time of a signal measured using a CRDS system is obtained by any of the four algorithms described above, and then Eqs. (11) and (12) are used to determine the substance concentration, $\chi$. In these embodiments, the resolution of the decay lifetime measurement determines the absorption sensitivity of the system.

Figure 15:
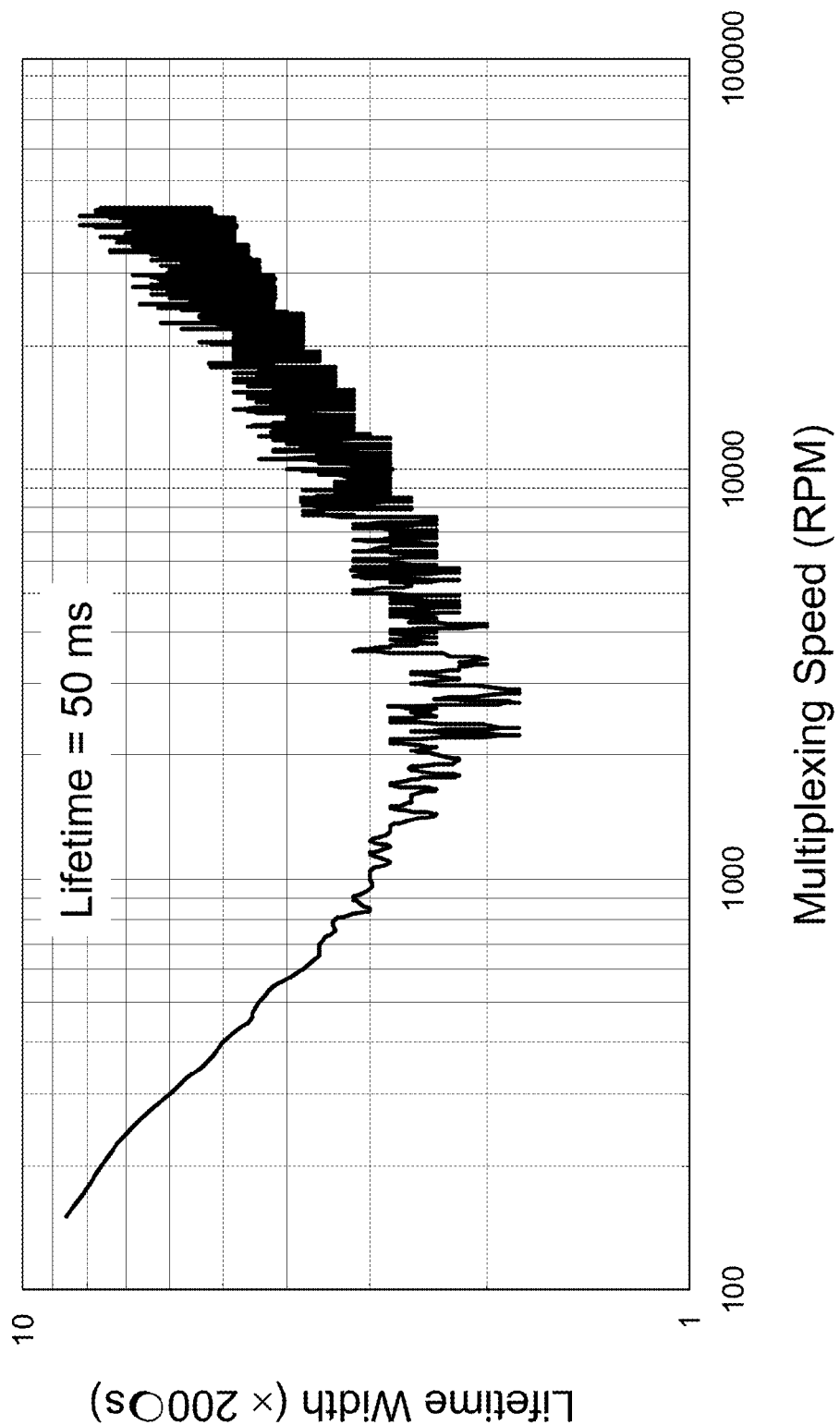
FIG. 15 shows a simulated result for the lifetime width as a function of multiplexing speed in the measurement of a time-decaying signal as disclosed in some embodiments of the present invention.

FIG. 15 shows, for different values of detector noise level, the dependence of the lifetime width as a function of the speed of the time-division multiplexing device. The results are simulated for a system that has a decay lifetime of $\tau = 50$ ms, and a time-division multiplexing device as in the embodiment described in FIG. 1, using 25 optical channels in a rotary switch of the RadiaLight® type operating as a time-division multiplexer 50. The lifetime width is calculated from the time segment of the variance function—cf. Eq. (15) in U.S. patent application Ser. No. 11/603,939, and FIG. 5—such that the value of the variance function is within 80% of its peak value. The uncertainty of the lifetime measurement is usually measured as the full-width, half maximum (FWHM) of the function peak, which is about 2.5 times smaller than the value plotted on the abscissa in FIG. 15. The curve is a characteristic 'Allan variance' plot, demonstrating that the reduction of measurement uncertainty by the increase of time-multiplexing speed has a limit at a certain value of the time-division multiplexing speed. Beyond this maximal time-division speed, the resulting uncertainty in lifetime measurements starts drifting up to higher values.

Figure 16:
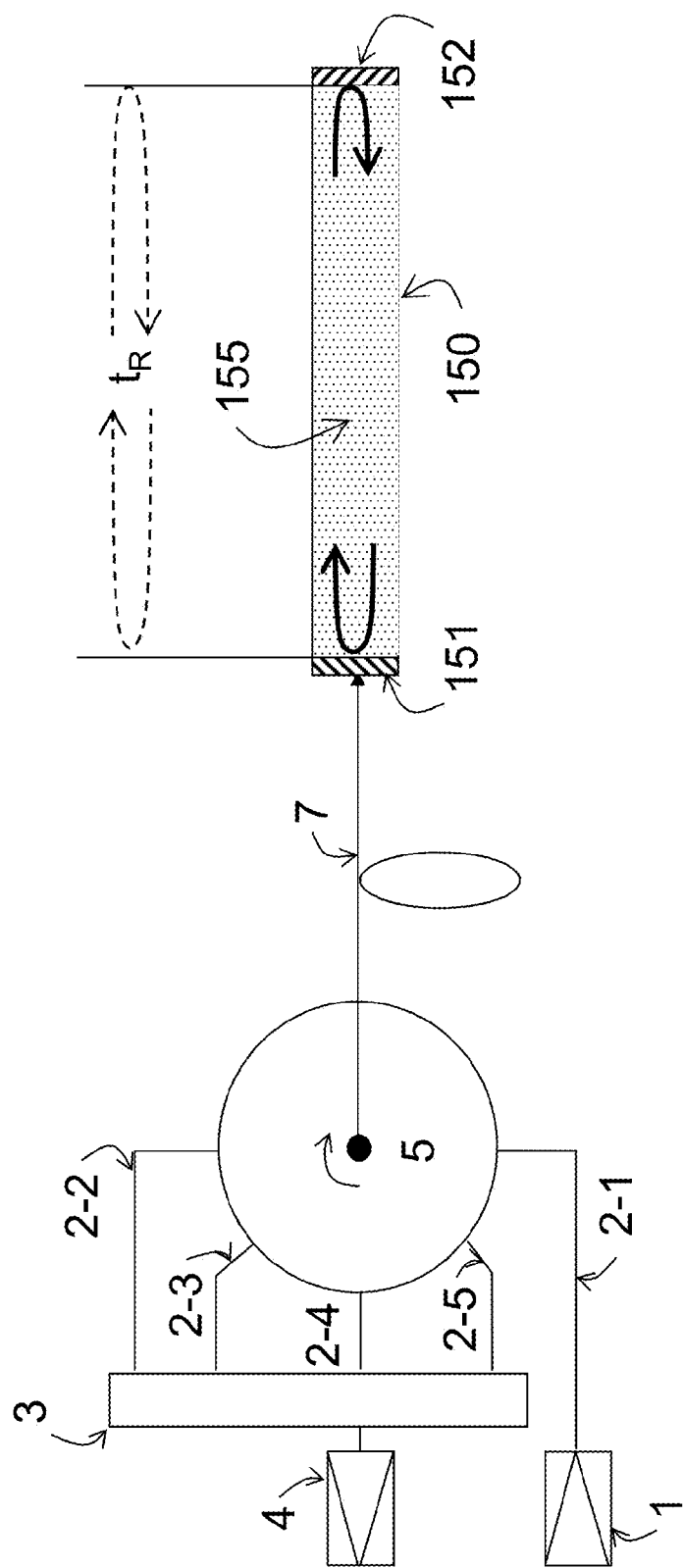
FIG. 16 shows a time-division multiplexing system used in conjunction with a cavity ring-down spectroscopy system whereby a light source is sent into a resonant cavity chamber filled with a sample gas composed by a mixture of absorbing compounds.

FIG. 16 shows an embodiment of the present invention where a CRDS system 150 is coupled to a time-division multiplexing system. The time-division multiplexing system 50 includes a light source 1, which in some embodiments may be a monochromatic laser, a light emitting diode (LED), or a lamp; also included is a detector 4, a time-division multiplexing element 5, which in some embodiments may be a rotary switch employing a reflecting prism as switching element, as described in the RadiaLight® rotary switch of U.S. Pat. No. 7,298,538; waveguides 2-1, 2-2, 2-3, 2-4, and 2-5, to couple light source 1 and detector 4 to switching element 5; multiplexer 3 to couple optical channels 2-2, 2-3, 2-4, and 2-5 into detector 4, and waveguide 7. In the embodiments depicted in FIG. 16, waveguide 7 acts as a probe to both deliver the light source into CRDS system 150, and retrieve the transmitted signal as a function of time.

The CRDS system 150 includes mirrors 151 and 152 with a selected reflectivity each R1 (mirror 151) and R2 (mirror 152). Inside the cavity, sample 155 is placed containing a mixture of different absorbing species. Samples can be in solid, liquid, gaseous, or plasma state, and the different absorbing species contained in the sample may be pure substances as in any of the chemical elements, or molecules, or clusters of molecules, or other types of chemical materials like nanostructures or microscopic arrays of molecules. In some embodiments of the present invention, the reflectivity of mirrors 151 and 152 is such that R1<R2, and R2 has a value very close to 1, ideally equal to 1. Some embodiments may include a mirror R2 with a reflectivity of 0.9999, or better. Other embodiments may further use a mirror 151 with reflectivity R1 equal to 0.98, 0.90, or less. The lower reflectivity of mirror 151 in some embodiments is convenient in order to obtain a sizeable signal returned back to the time-division multiplexing measurement device.

The time for a roundtrip travel of an optical pulse in CRDS system 150 is $t_R$. In some embodiments of the present invention, $t_R$ is lower than dwell time, $\Delta T$, so that multiple pulses coming from CRDS system 150 can be measured by a single optical channel 2-2, 2-3, 2-4, and 2-5. In some embodiments, roundtrip time $t_R$ is smaller than $1/10^{th}$ of $\Delta T$.

Other embodiments of this invention will be obvious to those skilled in the art in view of the above descriptions. For example, some embodiments use non-fluorescent samples having fluorophores attached to them, some other embodiments use intrinsically fluorescent samples. The above descriptions are meant to be illustrative and not limiting.

In some embodiments of the present invention, such as the one depicted in FIG. 16, light source 1 may be a continuous wave (CW) emitting source, and time division multiplexing 50 automatically creates a pulsed signal going into CRDS system 150, thus reducing the cost associated with an intrinsic pulsed light source. In some embodiments, such as the one depicted in FIG. 16, the optical output from CRDS system 150 is automatically de-coupled from light source 1, because once the initial light pulse completes a roundtrip through CRDS system 150, switching element 5 has decoupled the CRDS system 150 from light source 1. This eliminates the need to introduce bulky optical elements such as an isolator in front of light source 1.

Other embodiments of the present invention may use a pulsed light source 1 before time-division multiplexer 50. Further, some embodiments may include a light source 1 separated from time-division multiplexer 50, directly sending light to CRDS system 150 and the light collected out of CRDS system 150 being coupled into time-division multiplexer 50, multiplexer 3, and detector 4.

What is claimed is:

1. A cavity ring-down spectroscopy system, comprising:
   a light source for producing light to be directed at a sample, the sample comprising at least one light absorbing component;
   a ring-down cavity having a length between two reflective surfaces, the ring-down cavity including the sample;
   a time-division multiplexing device for transmitting the light to the ring-down cavity, and for collecting radiation transmitted by the sample at a plurality of pre-selected time intervals; and
   a detector for detecting the collected radiation at the plurality of pre-selected time intervals, wherein the plurality of pre-selected time intervals is determined by a roundtrip time of the radiation between two reflective surfaces in the ring-down cavity.

2. The system of claim 1, wherein at least one of the two reflective surfaces is partially reflective.

3. The system of claim 1, wherein the time-division multiplexing device comprises a gap between an optical channel for directing light from a light source at a sample and a first optical collection channel.

4. The system of claim 1, wherein the time-division multiplexing device comprises an optical element rotating at a rotational speed selected according to the plurality of pre-selected time intervals.

5. The system of claim 4, wherein the optical element is configured to rotate at different rotational speeds according to the plurality of pre-selected time intervals.

6. The system of claim 4, wherein the rotational speed is selected to obtain a reduced error in a measurement of the concentration of the sample in the ring-down cavity.

7. The system of claim 1, further comprising an electronic circuit to provide a reference decay signal having an amplitude and a decay time, wherein the electronic circuit is configured to scan the amplitude and to scan the decay time to find a concentration of the sample in the ring-down cavity.

8. The system of claim 4, wherein the rotational speed is adjusted to three different speeds to collect data forming a discrete Laplace transform of a decay function to obtain a concentration of the in the ring-down cavity.

9. The system of claim 4, wherein the rotational speed is scanned continuously between two limiting values to collect data forming a continuous Laplace transform of a decay function to obtain a concentration of the sample in the ring-down cavity.

10. The system of claim 9, wherein the two limiting values are selected to reduce an overlap in the signal between two contiguous optical channels in the time division multiplexing device.

11. The system of claim 4, wherein the rotational speed is selected according to a lifetime width of a decay measurement of a signal resulting from the sample in the ring-down cavity.

* * * * *